(12) United States Patent
Fukai et al.

(10) Patent No.: US 10,687,780 B2
(45) Date of Patent: Jun. 23, 2020

(54) ULTRASONOGRAPH

(75) Inventors: Seiichi Fukai, Kanagawa (JP);
Masahiro Saito, Kanagawa (JP);
Takashi Sakai, Kanagawa (JP); Yukiko Okamoto, Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 1023 days.

(21) Appl. No.: 12/867,600

(22) PCT Filed: Mar. 2, 2009

(86) PCT No.: PCT/JP2009/000933
§ 371 (c)(1),
(2), (4) Date: Aug. 13, 2010

(87) PCT Pub. No.: WO2009/110211
PCT Pub. Date: Sep. 11, 2009

(65) Prior Publication Data
US 2010/0321324 A1    Dec. 23, 2010

(30) Foreign Application Priority Data

Mar. 3, 2008 (JP) .................................. 2008-051794
Mar. 7, 2008 (JP) .................................. 2008-057117
(Continued)

(51) Int. Cl.
*A61B 8/00* (2006.01)
*G06F 3/0488* (2013.01)
*G06F 3/048* (2013.01)

(52) U.S. Cl.
CPC .............. *A61B 8/00* (2013.01); *A61B 8/465* (2013.01); *A61B 8/467* (2013.01); *A61B 8/469* (2013.01);
(Continued)

(58) Field of Classification Search
CPC ....... A61B 8/467; A61B 8/465; A61B 5/7435; A61B 6/465; A61B 8/462; A61B 8/469;
(Continued)

(56) References Cited

U.S. PATENT DOCUMENTS 6,063,030 A * 5/2000 Vara et al. .................... 600/437
8,094,901 B1 * 1/2012 Reicher et al. ............... 382/128
(Continued)

FOREIGN PATENT DOCUMENTS

FR       2861192 A1 * 4/2005  ............ A61B 8/465
JP     10-248843 A     9/1998
(Continued)

OTHER PUBLICATIONS

International Search Report for Appl. No. PCT/JP2009/000933 dated Jun. 9, 2009.
(Continued)

*Primary Examiner* — James M Kish
(74) *Attorney, Agent, or Firm* — Holtz, Holtz & Volek PC

(57) ABSTRACT

Disclosed is a technology that prevents a part of a touch panel-equipped display displaying an ultrasonic tomographic image from getting dirty with a fingerprint or scratch when using a drag operation to change the content of the ultrasonic tomographic image displayed on the touch panel-equipped display. According to this technology, the display screen is divided into an ultrasonic image area A1 which displays an ultrasonic image P and an operating part display area A2 which displays buttons (Fov, Pos, ROI, and Dop) for selecting a change to be made in the ultrasonic image P. The operating part display area A2 has a touch panel, and when a finger F selectively touches one of the displayed buttons and is dragged, the displayed image P of the ultrasonic image area A1 is changed on the apparatus side according to the selected changes and drag direction.

1 Claim, 20 Drawing Sheets

(30) Foreign Application Priority Data

Mar. 13, 2008 (JP) ................................ 2008-063431
Dec. 22, 2008 (JP) ................................ 2008-325720

(52) U.S. Cl.
 CPC .......... *G06F 3/048* (2013.01); *G06F 3/04883* (2013.01); *A61B 8/463* (2013.01); *G06T 2200/24* (2013.01)

(58) Field of Classification Search
 CPC .. G06F 19/3406; G06F 3/0488; G06F 1/1647; G06F 3/04847; G06F 3/04855; G06F 3/048; G06T 2200/24
 USPC .......................................... 600/437; 345/173
 See application file for complete search history.

(56) References Cited

U.S. PATENT DOCUMENTS

| | | | | |
|---|---|---|---|---|
| 2002/0026865 | A1* | 3/2002 | Akahori | G09B 15/023 84/478 |
| 2002/0033850 | A1* | 3/2002 | Bates | G06F 3/0481 715/853 |
| 2002/0087061 | A1 | 7/2002 | Lifshitz et al. | |
| 2003/0073894 | A1* | 4/2003 | Chiang | A61B 8/546 600/407 |
| 2003/0105400 | A1 | 6/2003 | Yawata et al. | |
| 2004/0196267 | A1* | 10/2004 | Kawai | G06F 3/04842 345/173 |
| 2004/0207661 | A1* | 10/2004 | Akaki | 345/764 |
| 2006/0232567 | A1* | 10/2006 | Westerman | G06F 3/0235 345/173 |
| 2007/0075915 | A1* | 4/2007 | Cheon et al. | 345/1.1 |
| 2007/0103450 | A1* | 5/2007 | Tang | G06F 3/03547 345/173 |
| 2008/0004728 | A1 | 1/2008 | Essex et al. | |
| 2008/0117230 | A1* | 5/2008 | Wegenkittl et al. | 345/619 |
| 2011/0134517 | A1* | 6/2011 | Shirota | G02B 21/368 359/381 |

FOREIGN PATENT DOCUMENTS

| | | | |
|---|---|---|---|
| JP | 10-254622 | A | 9/1998 |
| JP | 2002-336250 | A | 11/2002 |
| JP | 2003-169798 | A | 6/2003 |
| JP | 2003-233454 | A | 8/2003 |
| JP | 2005-137747 | A | 6/2005 |
| JP | 2006-018582 | A | 1/2006 |
| JP | 2006018582 | A * | 1/2006 |
| JP | 2006-026256 | * | 2/2006 |
| JP | 2006-026256 | A | 2/2006 |
| JP | 2007-159922 | A | 6/2007 |
| JP | 2007-316760 | A | 12/2007 |
| JP | 2008-12304 | A | 1/2008 |
| JP | 2010-142563 | A | 7/2010 |
| KR | 10-2007-0021422 | A | 2/2007 |
| KR | 10-2007-0029366 | A | 3/2007 |
| WO | 2006/040697 | A1 | 4/2006 |
| WO | 2006/111871 | A1 | 10/2006 |

OTHER PUBLICATIONS

Office Action issued in Japanese Patent Application No. 2013-054899 dated Nov. 5, 2013.
Korean Office Action dated Feb. 27, 2014 (and English translation thereof) in counterpart Korean Application No. 10-2010-7019703.
Japanese Office Action for Application No. JP 2008-057117 dated Jan. 22, 2013.
Extended European Search Report dated Nov. 6, 2014 issued in counterpart European Application No. 09716933.8.

* cited by examiner

STOP

ULTRASONOGRAPH

TECHNICAL FIELD

The present invention relates to an ultrasonograph including a touch panel-equipped display.

Moreover, the present invention relates to an ultrasonograph in which the content of an ultrasonic tomographic image displayed on a touch panel-equipped display can be changed using a drag operation.

Furthermore, the present invention relates to an ultrasonograph in which movement of a mouse cursor displayed on a touch panel-equipped display and the content of an ultrasonic tomographic image displayed thereon can be changed using a drag operation.

Still furthermore, the present invention relates to an ultrasonograph in which various types of image parameters of an ultrasonographic image displayed on a touch panel-equipped display can be changed.

BACKGROUND ART

One of the conventional techniques of an ultrasonograph including a touch panel-equipped display is described in Patent Document 1 below. FIG. 24 shows a conventional display example in which a drag operation is used to change the content of an ultrasonic tomographic image displayed on the touch panel-equipped display. The display screen is divided into an ultrasonic image area A1 which displays an ultrasonic image P and an operating part display area A2 which displays buttons for selection of a change of the ultrasonic image P (Gain, Depth, Color, Dop, and M in the drawing). When the operator touches the ultrasonic image area A1 with a finger F and drags after selecting a desired change by selectively touching one of the buttons displayed in the operating part display area A2, the display image P is changed according to the selected change and the drag direction. Another way of drag can be also used in measurement of the distance between the drag start position and the drag end position (for example, fetal head size) and the like.

A conventional ultrasonograph in which various image parameters of the ultrasonographic image displayed on a monitor can be changed with input devices includes: a monitor which displays a diagnostic image together with names and values of setting parameters; and various types of input devices for changing the image parameters. The input devices generally include hard keys such as a trackball, a key switch, a slide resistor, and an encoder knob and further include an input device provided with a multipurpose touch panel as a sub-display (see Patent Document 2) or a monitor provided with a touch panel so that input and display of images are performed on a same plane (see Patent Documents 3 and 4).
Patent Document 1: Japanese Patent Application Publication No. 2003-169798 (paragraph No. 0042)
Patent Document 2: Japanese Patent Application Publication No. H10-248843 (FIG. 1)
Patent Document 3: Japanese Patent Application Publication No. 2002-336250 (FIG. 3)
Patent Document 4: Japanese Patent Application Publication No. 2006-26256 (FIG. 2)

However, in the aforementioned conventional technique shown in FIG. 24, the finger F touches the ultrasonic image area A1 of the display screen and is dragged thereon. Accordingly, the ultrasonic image area A1 gets dirty with a fingerprint FP or a scratch D, thus making it hard to see the ultrasonic image P.

DISCLOSURE OF THE INVENTION

In the light of the aforementioned problem of the conventional techniques, an object of the present invention is to provide an ultrasonograph which is prevented from getting dirty in a part of a touch panel-equipped display displaying an ultrasonic image with a fingerprint or scratch when the drag operation is used to change the content of the ultrasonic tomographic image displayed thereon and which makes the ultrasonic tomographic image more visible.

Moreover, the conventional ultrasonograph including a touch panel as an input device has the following problems. When intuitive input is performed by sliding a finger or the like on an entry area arranged vertically or horizontally, it is difficult to perform input in a linear fashion. The entry area is a part of the screen and is small, where the operation is difficult to perform. Furthermore, in the conventional ultrasonograph including the above described hard keys as the input devices, vertical or horizontal scroll using a trackball, which has high operational flexibility, has difficulties in keeping a desired speed or controlling the position. Moreover, the trackball needs to be rolled several times for one operation and also has a problem in such an inconvenient operation.

The present invention is made to solve the conventional problems. An object of the present invention is to provide an ultrasonograph in which the operability in adjusting various image parameters is improved by using as a touch pad an area of a touch panel adjacent to a monitor frame, and allowing a finger or a tool to slide on the area vertically or horizontally along the monitor frame as input means.

In order to achieve the above object, an ultrasonograph of the present invention comprises: an ultrasonic signal transmitter/receiver transmitting and receiving an ultrasonic signal through an ultrasonic probe; an image processing unit converting the ultrasonic signal received by the ultrasonic signal transmitter/receiver into an ultrasonic image; a display including: a first display area displaying the ultrasonic image converted by the image processing unit; and a second display area displaying operation buttons for changing display content of the ultrasonic image displayed in the first display area, the display including a touch panel at least on the second display area; and display control means which, when one of the operation buttons displayed in the second display area is touched and drag motion is made on the touch panel, changes the display content of the ultrasonic image displayed in the first display area based on a rule set for each of the operation buttons.

In addition, in order to achieve the above object, an ultrasonograph of the present invention comprises: an ultrasonic signal transmitter/receiver transmitting and receiving an ultrasonic signal through an ultrasonic probe; an image processing unit converting the ultrasonic signal received by the ultrasonic signal transmitter/receiver into an ultrasonic image; a display including: a first display area displaying the ultrasonic image converted by the image processing unit; and a second display area displaying an icon for making a change instruction of the display content of the ultrasonic image displayed in the first display area and a drag area on which a drag operation is performed to change the direction of the display change, the display including a touch panel at least on the second display area; and display control means which, when the icon is touched, displays the icon in the drag area and, when drag motion is made on the drag area, changes the ultrasonic image displayed in the first display area according to the change instruction of the icon and the drag direction in the drag area. With such a configuration, the drag motion is performed on the second display area which displays the operating buttons but not on the first display area which displays the ultrasonic image. Accordingly, it is possible to prevent a part of the display displaying the ultrasonic tomographic image from getting dirty with fingerprints and scratches, thus making the ultrasonic tomographic image more visible.

Moreover, the ultrasonograph has a configuration wherein the display control means enables the drag operation even when the drag operation is performed from a drag start position in the drag area to a drag end position outside of the drag area on the touch panel.

Further, the ultrasonograph has a configuration wherein when a different operation button is touched while the drag operation is being performed on the touch panel from the operation button or a position in the drag area, the display control means disables a touch operation for the different operation button.

Furthermore, the ultrasonograph has a configuration wherein when the drag operation is finished after disabling the touch operation for the different operation button, the display control means enables the disabled touch operation for the different operation button.
With such a configuration, it is possible to secure the flexibility in arrangement positions of the operating buttons or drag area for changing the display content of the ultrasonic image and the other operating buttons.

Additionally, the ultrasonograph has a configuration wherein when drag motion is started from the drag area and then is continuously stopped at an edge of the drag area, the display control means continues moving a cursor.

Also, the ultrasonograph has a configuration wherein the display control means moves a cursor upon a drag operation in which a finger slides on the drag area.

In addition, the ultrasonograph has a configuration wherein when the first display area is touched, the display control means alerts an operator by displaying a warning message on the display screen not to touch the first display area or by causing the second display area to flash or change in brightness.

Moreover, the ultrasonograph further comprises calculating means calculating a distance between start and end points of a mouse cursor moved by the drag operation in the ultrasonic image, and has a configuration wherein the display control means displays the distance in the ultrasonic image calculated by the calculating means in the first or second display area.

Further, the ultrasonograph has a configuration wherein the display control means displays a finger image in the drag area as a guide for the drag operation together with the icon.

Furthermore, the ultrasonograph has a configuration wherein the display includes an outer frame around the display screen, and the second display area includes independent function areas at respective sides of an adjacent portion inwardly adjacent to the outer frame, functions independent of each other being assignable to the independent function areas. With such a configuration, the operator can easily improve the operability at adjusting various types of image parameters of the ultrasonograph using the individual sides of the outer frame of the monitor.

Additionally, the ultrasonograph has a configuration wherein the display control means is a controller capable of detecting a coordinate position of a specified point in any of the independent function areas pointed by an operator for the touch panel, and detecting moving speed or acceleration of the specified point to output a signal thereof. With such a configuration, when input is made by a finger or a tool sliding on the touch panel area provided along the monitor frame, the input can be stably performed in various operation patterns, thus improving the operability.

Also, the ultrasonograph has a configuration wherein the display control means is a controller capable of changing parameters expressed as continuous, discrete, or binary values with an operation in any of the independent function areas. With such a configuration, it is possible to change image parameters with a wide variety of features in the independent function area.

Moreover, the ultrasonograph has a configuration wherein the display control means is a controller capable of detecting a relative or absolute position of the specified point in any of the independent function areas with respect to length of the outer frame or detecting an absolute or relative amount of movement of the specified point. With such a configuration, the independent function area can vary the way of adjusting the image parameters. Accordingly, the image parameters can be adjusted with a method suitable to each parameter.

Further, the ultrasonograph has a configuration wherein the controller allows the functions assigned to the independent function areas to be changed individually or collectively for the individual sides of the outer frame. With such a configuration, the functions assigned to the independent function area can be easily changed, and the wide variety of operations of changing parameters can be therefore performed in this area.

Furthermore, the ultrasonograph has a configuration wherein information on the function assigned to the independent function area adjacent to each side of the outer frame is displayed at the independent function area. With such a configuration, the user can easily check the function assigned to the touch panel area provided along the monitor frame.

According to the present invention, it is possible to prevent a part of a touch panel-equipped display which displays an ultrasonic tomographic image from getting dirty with fingerprints or scratches when a drag operation is used to change the displayed content of the ultrasonic tomographic image displayed on the touch panel-equipped display. Furthermore, the ultrasonic tomographic image can be made more visible.

Moreover, the present invention allows part of the touch panel area adjacent to the outer frame of the monitor to be treated as touch pads having independent functions set thereto. Sliding a finger or a tool as input means on each area along the outer frame of the monitor facilitates adjustment of the input speed and position. It is therefore possible to provide an ultrasonograph having an effect on allowing input to be performed by various institutive operation ways.

BEST MODE FOR CARRYING OUT THE INVENTION

Hereinafter, embodiments of the present invention are described with reference to the drawings.

First Embodiment

Figure 1:
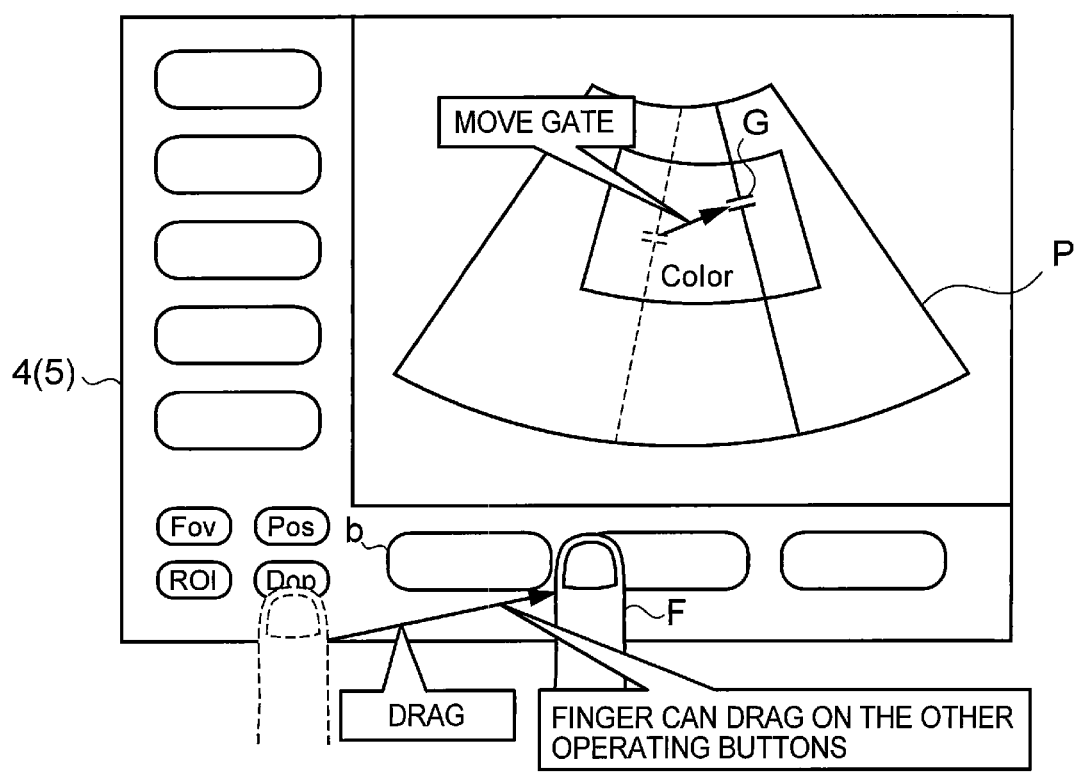
FIG. 1 is an explanatory view showing a display example of a first embodiment of an ultrasonograph according to the present invention.

FIG. 1 is an explanatory view showing a display example of a first embodiment of an ultrasonograph according to the present invention. The display screen shown in FIG. 1 is divided into an ultrasonic image area A1 which displays an ultrasonic image P and an operating part display area A2 which displays displayed-content change buttons for selecting a change to be performed for the ultrasonic image P (for example, Fov, Pos, ROI, and Dop in the drawing) (hereinafter, also referred to as just buttons) similarly to the prior art and differs from the prior art in the following points.

First, the ultrasonic image area A1 displays only the ultrasonic image P. The ultrasonic image P does not change even if the ultrasonic image area A1 is touched for the purpose of image change according to the present invention. The ultrasonic image area A1 does not need to be provided with the touch panel but may be provided with the touch panel for another purpose. Furthermore, the operating part display area A2 is equipped with a touch panel. When a finger F selectively touches one of the displayed displayed-content change buttons (Fov, Pos, ROI, and Dop in the drawing) and is dragged, the display image P in the ultrasonic image area A1 is changed according to the selected change and the drag direction on the apparatus side. Even if another button b is touched during the drag, the touch operation is disabled on the apparatus side. It is therefore possible to prevent the ultrasonic image area A from getting dirty with fingerprints or scratches, thus making the ultrasonic tomographic image more visible.

Herein, the examples of buttons for changing the display image P in the ultrasonic image area A1 are described in FIG. 1.

(1) Fov (Field of View): to change an angle of the display image P of the ultrasonic image area A1 in the one-dimensional scanning direction (2) Pos (Position): to change the position of the display image P of the ultrasonic image area A1 in the one-dimensional scanning direction (3) ROI (Region of Interest): to change the size and position of the display image P of the ultrasonic image area A1 in the two-dimensional direction and display the display image P in color (4) Dop (Doppler): to move the position of a Doppler sampling gate of the display image P of the ultrasonic image area A1.

FIG. 1 shows an operation of the above (4) in moving the position of a Doppler sampling gate G of the display image P in the ultrasonic image area A1, showing the case where the finger F touches the Dop button displayed in the operating part display area A2 and is then dragged to the right. Herein, the Dop button is previously defined and set so that a horizontal drag at the Dop button moves the position of the Doppler sampling gate G in the same direction. According to this rule, the position of the Doppler sampling gate G of the display image P of the ultrasonic image area A1 is moved according to the drag direction on the apparatus side. Moreover, although the button b as a button of another function is touched during the drag, the touch operation on the button b is disabled. This allows a drag over the button b from the position of the Dop button. Furthermore, when the touch panel stops being touched during the drag, it is judged that the operation of the Dop button is finished, and the disabled touch operation for the button b is enabled. The rules set for individual buttons can change operations including moving the object image to the right and left and up and down, increasing or reducing the width of the image, and zooming up and down the entire image.

Figure 2:
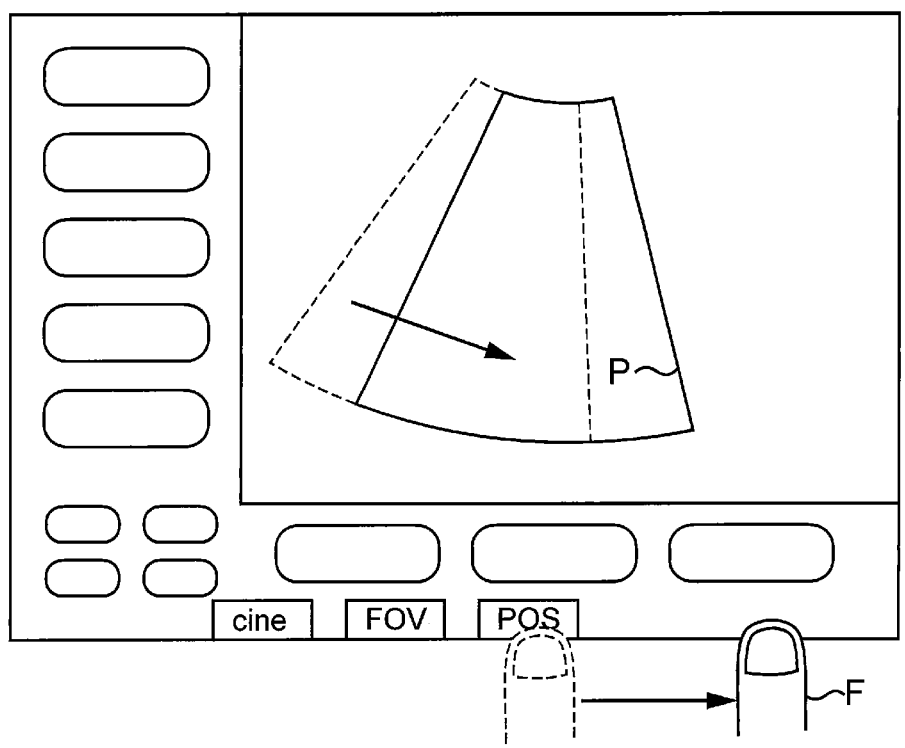
FIG. 2 is an explanatory view showing another display example of the first embodiment of the ultrasonograph according to the present invention.
Figure 3:
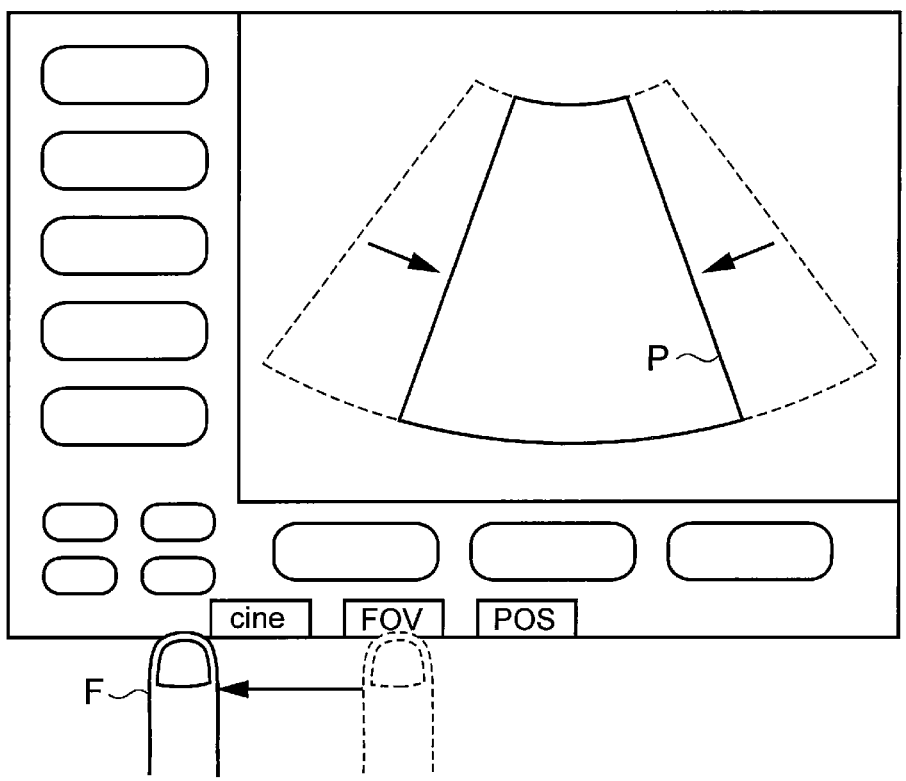
FIG. 3 is an explanatory view showing still another display example of the first embodiment of the ultrasonograph according to the present invention.

FIGS. 2 and 3 show other display examples of the buttons in the operating part display area A2. FIG. 2 shows an operation of above (2) in changing the position of the display image P of the ultrasonic image area A1 in the one-dimensional scanning direction. When the finger F touches the POS button displayed in the operating part display area A2 and is dragged horizontally, the position of the display image P in the ultrasonic image area A1 is changed from the position indicated by a dotted line to the position indicated by a solid line according to the drag direction on the apparatus side. FIG. 3 shows an operation of above (1) in changing the angle of the display image P of the ultrasonic image area A1 in the one-dimensional scanning direction. When the finger F touches the FOV button displayed in the operating part display area A2 and is dragged horizontally, the angle of the display image P (the angle of the sector) of the ultrasonic image area A1 is changed according to the drag direction on the apparatus side. Herein, the FOV button is defined so that a drag to the right causes "an increase in angle" while a drag to the left causes "a decrease in angle". In FIG. 3, the finger F is dragged to the left, and the sector with a large angle (with large width), which is indicated by the dotted line, is changed to the sector with a small angle (with small width), which is indicated by the solid line. Herein, since the drags for the POS and FOV buttons are only directed in the horizontal direction of the displayed image of the ultrasonic image area A1, the POS and FOV buttons are horizontally arranged at the bottom of the screen as an example.

Figure 4:
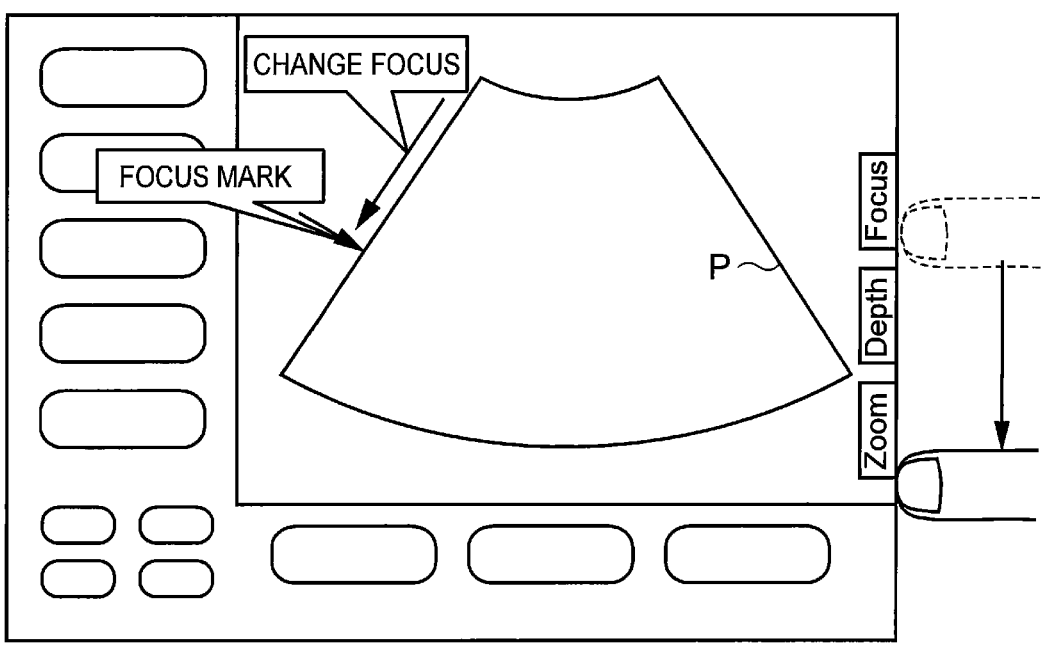
FIG. 4 is an explanatory view showing still another display example of the first embodiment of the ultrasonograph according to the present invention.

FIG. 4 shows another display example of the buttons in the operating part display area A2. The operating part display area A2 is provided with a Focus button for changing the focus position of the display image P in the ultrasonic image area A1, a Depth button for changing the depth of the display image P in the ultrasonic image area A1, and a Zoom button for zooming the display image P in the ultrasonic image area A1. The drags for these buttons are directed only in the vertical direction of the displayed image of the ultrasonic image area A1 and are therefore vertically arranged at the right edge of the screen as an example. Herein, the positions of the buttons are located in the ultrasonic image area A1 which is normally set so as not to include the buttons. The drawing shows the mode where the positions of these buttons can be changed using a dedicated key to a part of the ultrasonic image area A1 in which it is judged that the ultrasonic image P is not displayed (the right edge of the display may be initially fixed as the operating part display area). As shown in FIG. 4, a touch on the Focus button and a vertical drag changes the focus position of the display image P according to the drag direction on the apparatus side and moves a focus mark.

Figure 5:
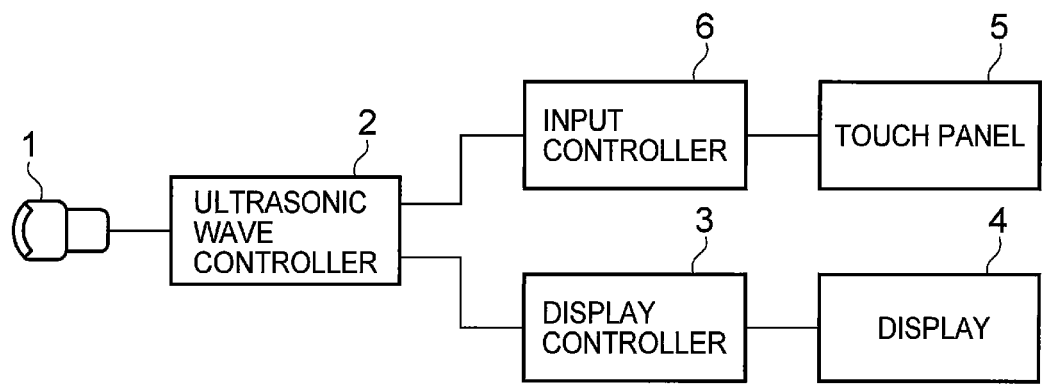
FIG. 5 is a block diagram showing a configuration of the first embodiment of the ultrasonograph according to the present invention.

FIG. 5 is a block diagram showing a configuration of the ultrasonograph executing the aforementioned display control. First, the touch panel-equipped display includes a display 4 and a touch panel 5. An ultrasonic wave controller 2 controls transmission of ultrasonic waves of an ultrasonic probe 1 and reception of reflected signals thereof. A display controller 3 processes the received reflected signal to display the ultrasonic image in the ultrasonic image area A1 of the display 4 as shown in FIGS. 1 to 4, and executes the display control to display the various operating buttons in the operating part display area A2. An input controller 6 detects a touch position on the touch panel 5, and the ultrasonic wave controller 2 executes control for changing the image in the ultrasonic image area A1 of the display 4 according to the touch position on the touch panel 5 which is detected by the input controller 6.

Figure 6:
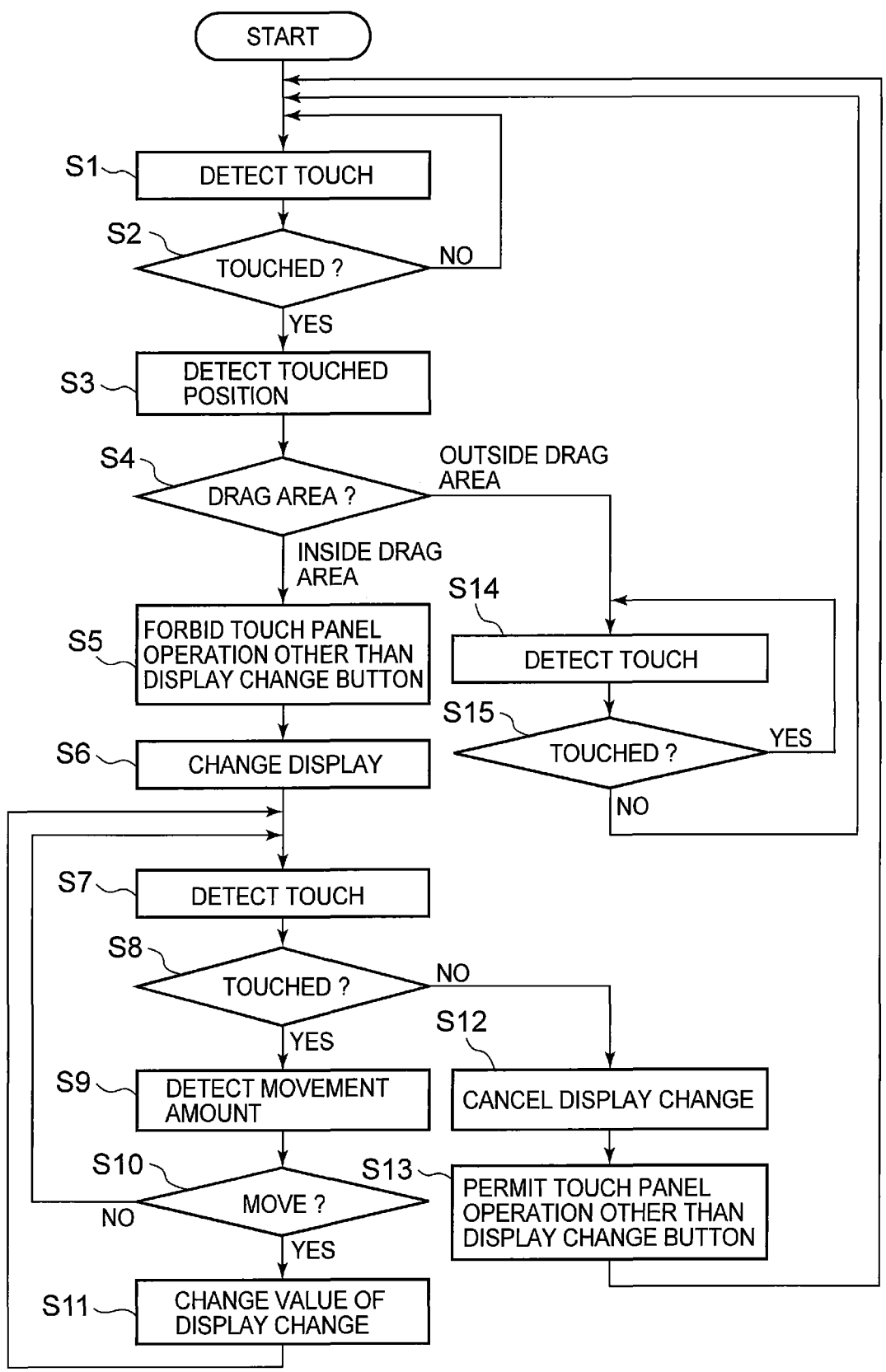
FIG. 6 is a flowchart for explaining an operation of the first embodiment of the ultrasonograph according to the present invention.

FIG. 6 is a flowchart for explaining the aforementioned display control. At first, a touch detection process is executed (step S1). If the touch panel 4 is not touched, the control returns to the step S1 from step S2, and if the touch panel 4 is touched, the control proceeds from the step S2 to step S3. In the step S3, the touch position is detected, and it is then checked whether the detected touch position is located in a drag area (step S4). If the detected touch position is located in the drag area, touch panel operations other than operations of the displayed-content change buttons are forbidden (step S5), and the change of the displayed-content change button touched for the operation is selected (step S6).

Subsequently, a touch detection function is activated for monitoring the touch state (step S7), and if the touch panel 4 is touched, the control proceeds from step S8 to step S9. In the step S9, the distance that the touch position is moved is detected. If there is movement of the touch position, the control proceeds from the step S10 to step S11. The value of the display change according to the movement distance is changed (the displayed state is changed), and the control then returns to the step S7. If there is no movement of the touch position in the step S10, the control returns to the step S7. Moreover, if the touch panel 4 is not touched in the step S8, the display change is canceled (step S12). Subsequently, the touch panel operations other than the operations for the displayed-content change buttons are permitted (step S13), and the control returns to the step S1. If the touch position is not located in the drag area in the step S4, the touch detection process is executed (step S14). If the touch panel is not touched, the control returns to the step S1 from step S15, and if the touch panel 4 is touched, the control proceeds from the step S15 to the step S14. With regard to the time to change the display state as described above, the displayed state may be changed after the movement of the touch position is completed as well as being changed in real time while the touch position is moving.

Second Embodiment

Figure 7:
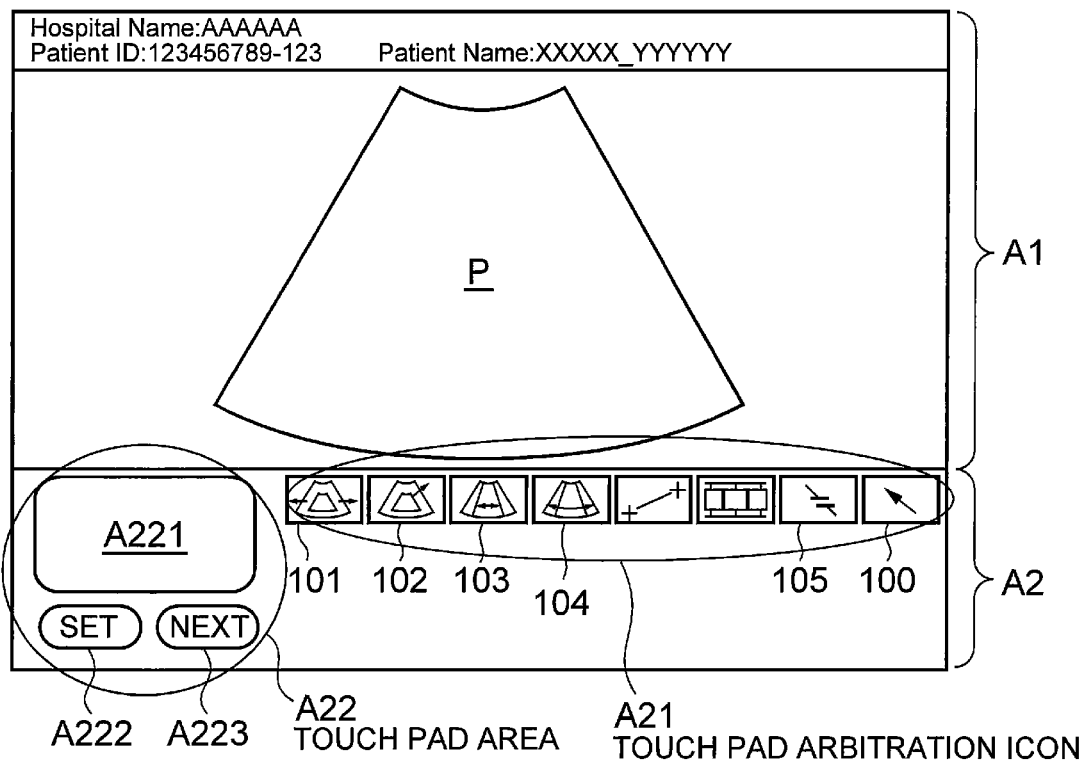
FIG. 7 is an explanatory view showing a display example of a second embodiment of the ultrasonograph according to the present invention.

FIG. 7 is an explanatory view showing a display example of a second embodiment of the ultrasonograph according to the present invention. The display screen shown in FIG. 7 is divided into an ultrasonic image area A1 which displays an ultrasonic image P and an operating part display area A2 used to specify the change to be performed for the ultrasonic image P similarly to the prior art and differs from the prior art in the following points.

First, the ultrasonic image area A1 as a first display area of the present invention displays only the ultrasonic image P. The ultrasonic image P does not change even if the ultrasonic image area A1 is touched for the image change according to the present invention. The ultrasonic image area A1 does not need to be provided with the touch panel but may be provided with the touch panel for another purpose. Furthermore, the operating part display area A2 as a second display area is provided with a touch panel. The operating part display area A2 displays a touch pad arbitration icon A21 for selecting a change to be performed for the ultrasonic image P and a touch pad area A22 including an icon display/drag area A221, a SET button A222, and a NEXT button A223. The touch pad arbitration icon A21 is composed of an icon 100 for moving a mouse cursor instead of a trackball and icons 101 to 105 representing multiple image changes. When any one of the icons 100 to 105 is selected by a touch operation, an icon of the selected change is displayed in the icon display/drag area A221 of the touch pad area A22. This makes it clear what the function of the icon display/drag area A221 is assigned to and improves the visibility from the operator. When a drag operation is performed on the icon display/drag area A221, the display image P in the ultrasonic image area A1 is changed according to the specification by the selected change and the drag direction on the apparatus side. It is therefore possible to prevent the ultrasonic image area A1 from getting dirty with fingerprints or scratches, thus making the ultrasonic tomographic image more visible.

Herein, examples of the change performed for the display image P in the ultrasonic image area A1 are described.

(1) Fov (Field of View): to change an angle of the display image P of the ultrasonic image area A1 in the one-dimensional scanning direction (2) Pos (Position): to change the position of the display image P of the ultrasonic image area A1 in the one-dimensional scanning direction (3) ROI (Region of Interest): to change two dimensional size and position of the display image P of the ultrasonic image area A1 and displays the display image P in color (4) Dop (Doppler): to move the position of a Doppler sampling gate of the display image P of the ultrasonic image area A1

The touch pad arbitration icon A21 shown in FIG. 7 is briefly described. The icon 101 is an ROI size icon changing the two dimensional size (ROI size) of the display image P of the ultrasonic image area A1. The icon 102 is a ROI pos icon changing the two-dimensional position (ROI position) of the display image P of the ultrasonic image area A1. The icon 103 is a POS icon changing the position of the display image P of the ultrasonic image area A1 in the one-dimensional scanning direction. The icon 104 is a Fov icon changing the angle of the display image P of the ultrasonic image area A1 in the one-dimensional scanning direction. Moreover, the icon 105 is a Dop icon changing the Doppler sampling gate of the display image P of the ultrasonic image area A1.

Figure 8A:
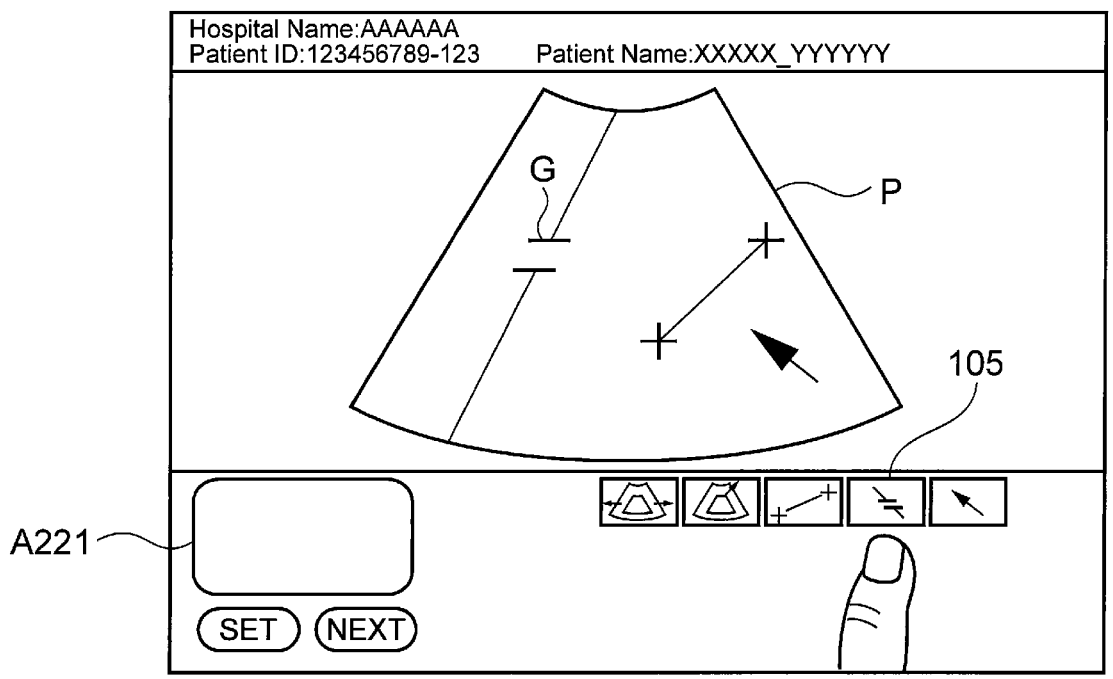
FIG. 8A is a first explanatory view showing a mode transition of the display example of the second embodiment of the ultrasonograph according to the present invention.
Figure 8B:
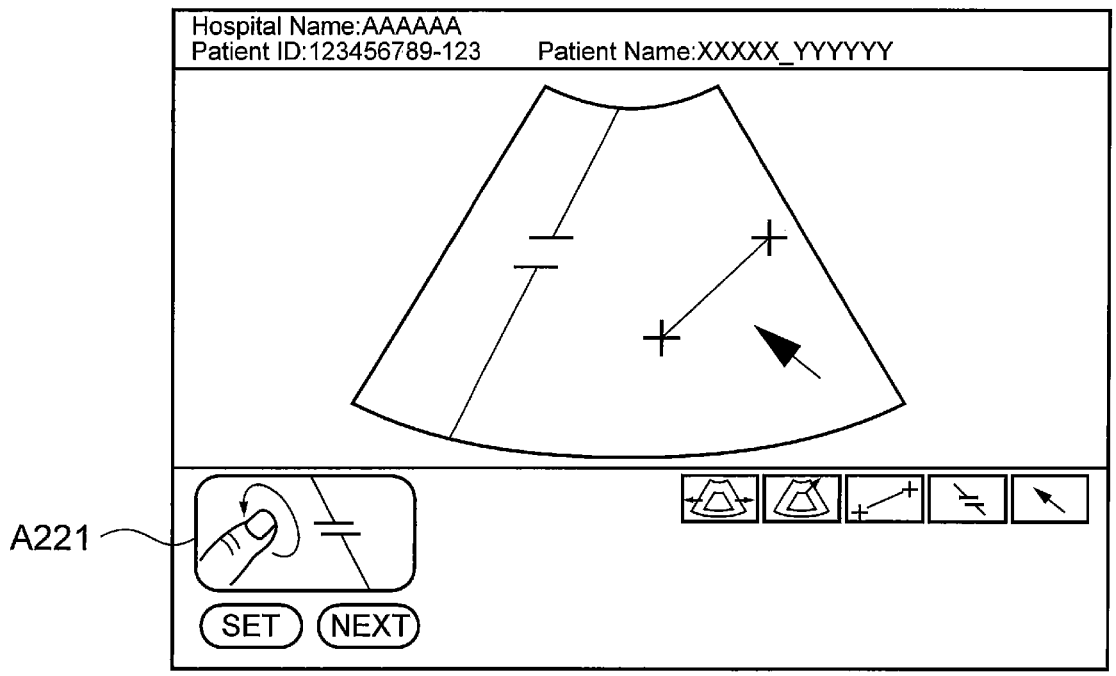
FIG. 8B is a second explanatory view showing the mode transition of the display example of the second embodiment of the ultrasonograph according to the present invention.
Figure 8C:
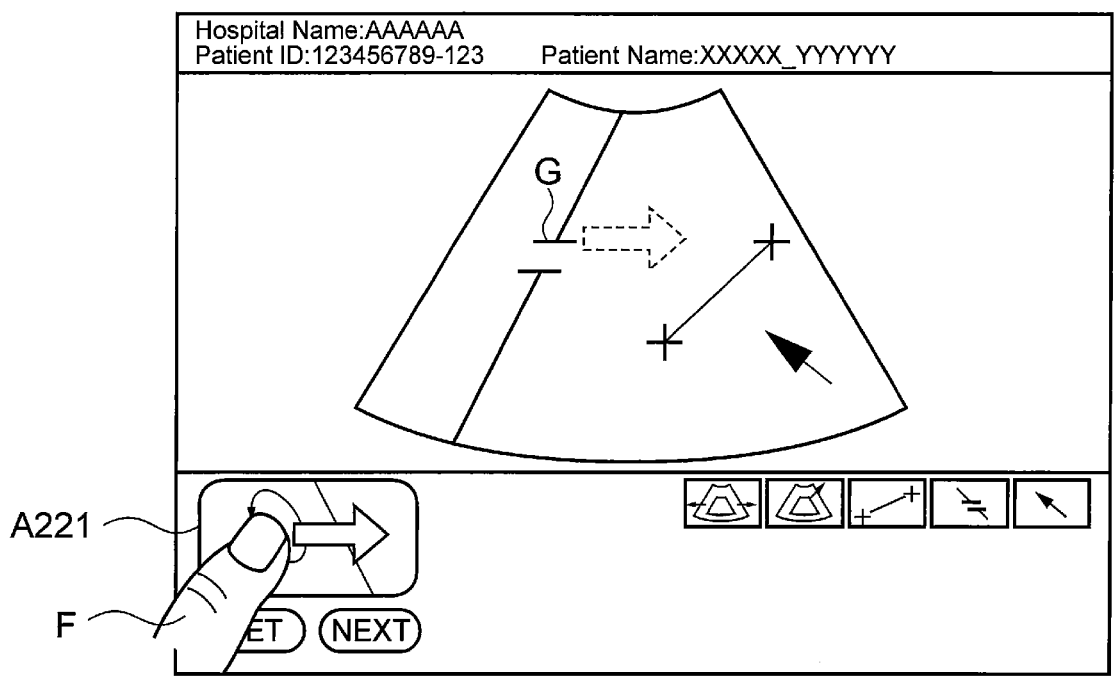
FIG. 8C is a third explanatory view showing the mode transition of the display example of the second embodiment of the ultrasonograph according to the present invention.
Figure 8D:
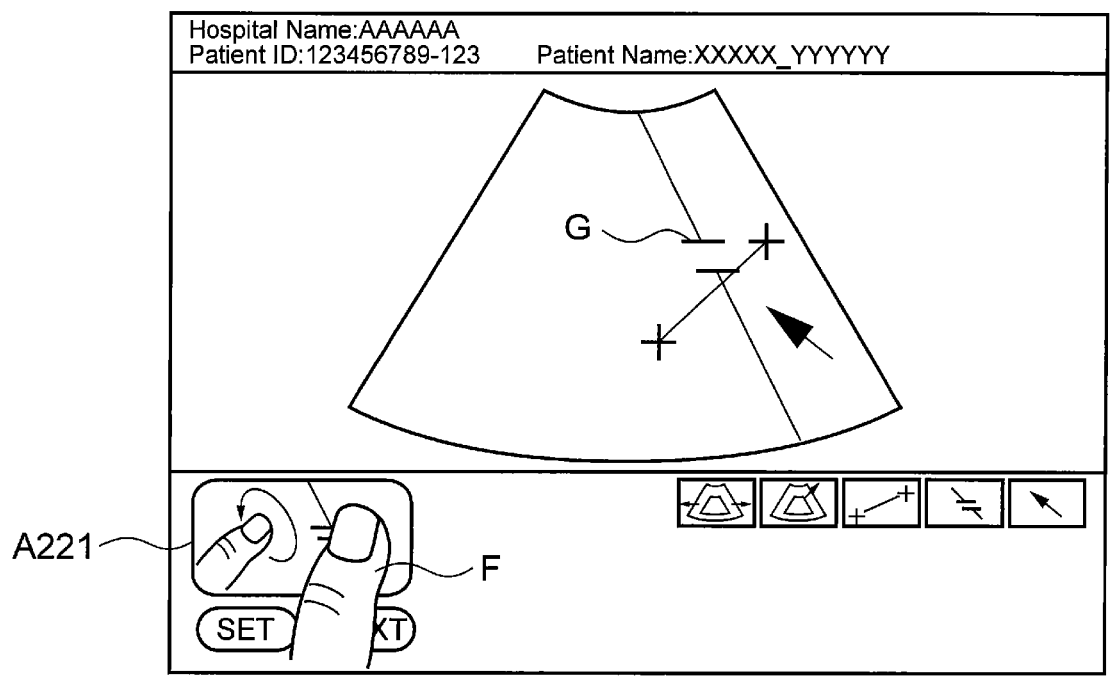
FIG. 8D is a fourth explanatory view showing the mode transition of the display example of the second embodiment of the ultrasonograph according to the present invention.

FIGS. 8A to 8D show the operation of the above (4) in the case of moving the position of the Doppler sampling gate G of the display image P of the ultrasonic image area A1. First, when the Dop icon 105 is touched in the touch pad arbitration icon A21 in a state where the icon display/drag area A221 is not assigned to any function as shown in FIG. 8A, an image same as the touched Dop icon 105 and a finger image as a drag operation guide are displayed in the icon display/drag area A221 as shown in FIG. 8B. Subsequently, as shown in FIGS. 8C and 8D, when the finger F is dragged on the icon display/drag area A221, the position of the Doppler sampling gate G of the display image P in the ultrasonic image area A1 is moved according to the drag direction on the apparatus side.

Figure 9:
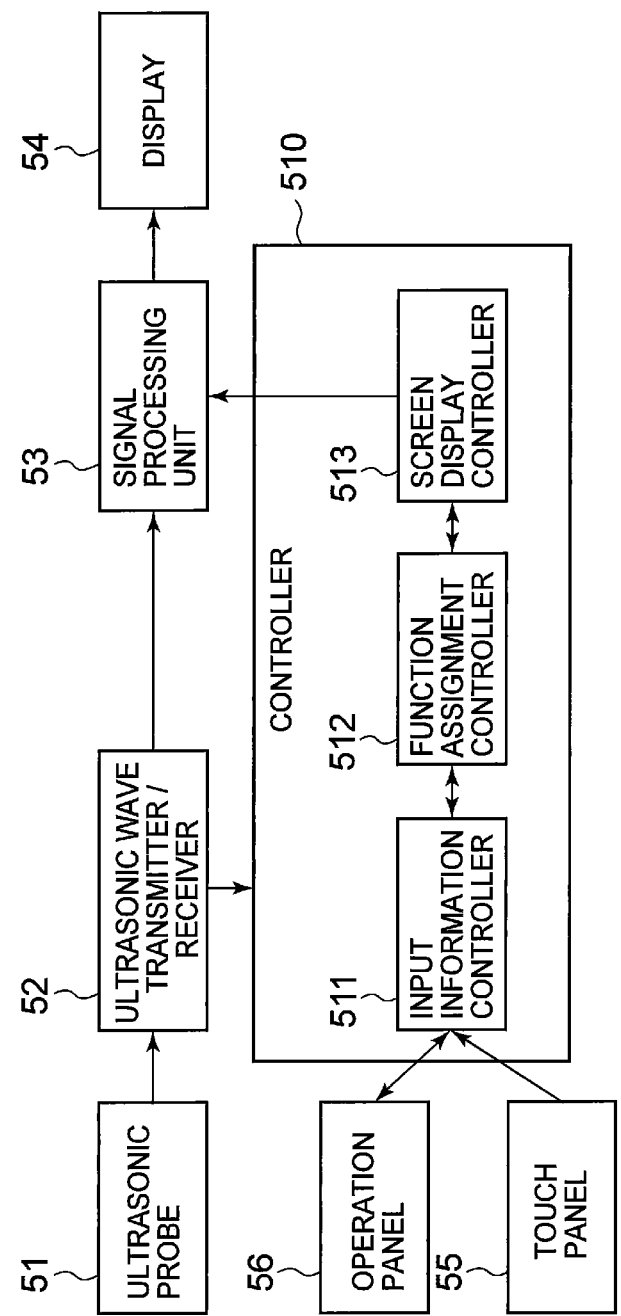
FIG. 9 is a block diagram showing a configuration of the second embodiment of the ultrasonograph according to the present invention.

FIG. 9 is a block diagram showing a configuration of the ultrasonograph executing the above display control. First, the touch panel-equipped display includes a display 54 and a touch panel 55. An ultrasonic wave controller 52 controls transmission of ultrasonic waves from an ultrasonic probe 51 and reception of the reflected signals. A signal processor 53 processes the received reflected signal to display the ultrasonic image P in the ultrasonic image area A1 of the display 54 as shown in FIGS. 7 and 8A to 8D and executes display control for displaying various operating buttons in the operating part display area A2. A controller 510 includes an input information controller 511, a function assignment controller 512, and a screen display controller 513. The input information controller 511 receives information (an event) of the user operation performed through the touch panel 55 and an operating panel 56 and processes the same. The function assignment controller 512 especially determines which function the touch pad area A22 is assigned to, and the screen display controller 513 especially executes the display control of changing icons to be displayed in the icon display/drag area A221 of the touch pad area A22. The controller 510 executes a control for changing the image in the ultrasonic image area A1 of the display 54 according to the drag direction in the icon display/drag area A221.

On the assumption that the operator accidentally touches the ultrasonic image area A1, when the ultrasonic image area A1 is touched, a warning message such as "Don't touch the ultrasonic image area A1! Operate in the operating part display area A2." is displayed on the display screen, or the operating part display area A2 flashes or changes in brightness, thus warning the operator and drawing his/her attention. This can further prevent the display part of the ultrasonic tomographic image from getting dirty with fingerprints or scratches, thus making the ultrasonic tomographic image more visible. Furthermore, identification information of an operator may be inputted at the start of the drag operation so that the warning level (flashing frequency, the amount of change in brightness) is raised for more attentions when a same operator accidentally touches the ultrasonic wave image area A1 several times for a predetermined period of time.

Third Embodiment

Figure 10:
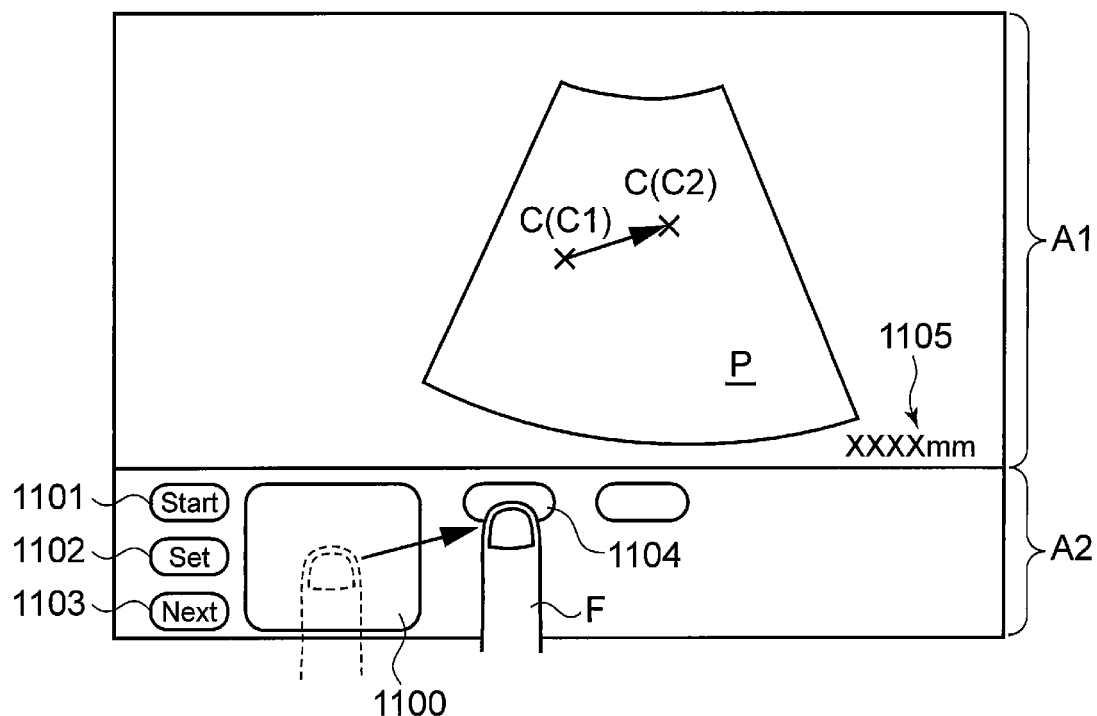
FIG. 10 is an explanatory view showing a display example of a third embodiment of the ultrasonograph according to the present invention.

FIG. 10 is an explanatory view showing a display example of a third embodiment of the ultrasonograph according to the present invention. The display screen shown in FIG. 10 is divided into an ultrasonic image area A1 which displays an ultrasonic image P and an operating part display area A2 used to perform a drag operation for the ultrasonic image P similarly to the prior art. First, the ultrasonic image area A1 as the first display area of the present invention displays only the ultrasonic image P and a cursor C. Even if the ultrasonic image area A1 is touched, the cursor C does not move. The ultrasonic image area A1 does not need to be provided with the touch panel but may be provided with the touch panel for another purpose.

Furthermore, the operating part display area A2 as a second display area is provided with a touch panel. The operating part display area A2 displays a touch pad area 1100 as a drag area used for moving the cursor C, a Start button 1101, a Set button 1102, a Next button 1103, a button 1104 for a different mode, and the like. When a finger F is dragged on the touch pad area 1100, the cursor C is moved according to the drag direction and distance on the apparatus side (C1→C2 in the drawing). It is therefore possible to prevent the ultrasonic image area A1 from getting dirty with fingerprints or scratches, thus making the ultrasonic image more visible.

Figure 11:
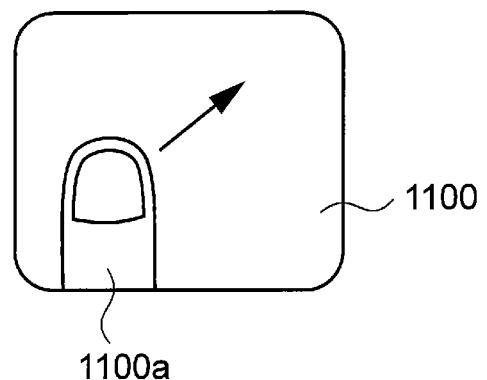
FIG. 11 is an explanatory view showing a display example of a touch pad area of FIG. 10.

As shown in FIG. 11, a finger image 1100a is displayed in the touch pad area 1100 as the drag area to remind the user not to drag on the ultrasonic image P. Moreover, on the assumption that the operator accidentally touches the ultrasonic image area A1, when the ultrasonic image area A1 is touched, a warning message such as "Don't touch the ultrasonic image area A1! Operate in the operating part display area A2." is displayed on the display screen, or the operating part display area A2 is configured to flash or change in brightness, thus warning the operator and drawing his/her attention. This can further prevent the part of the screen displaying the ultrasonic tomographic image from getting dirty with fingerprints or scratches, thus making the ultrasonic tomographic image more visible. Furthermore, identification information of an operator may be inputted at the start of the drag operation so that the warning level (flashing frequency, the amount of change in brightness) is raised for more attentions when a same operator accidentally touches the ultrasonic wave image area A1 several times for a predetermined period of time.

Herein, the drag operation is enabled not only in the touch pad area 1100 but also outside of the touch pad area 1100 as shown in FIG. 10. Herein, when the button 1104 for a different mode is touched while the drag operation is being performed outside of the touch pad area 1100, the touch operation for the button 1104 for a different mode is disabled, and the drag operation is enabled. At the end of the drag operation, the disabled touch operation for the button 1104 for the different mode is enabled again.

One of the applications of moving the cursor C displayed in the ultrasonic image A1 is measurement of size of the fetal head in a fetal image displayed in the ultrasonic image area A1. In this case, the user specifies both ends of the head of the fetal image (the start and end points) with the cursor C. When the both ends of the head are specified, the both ends of the head are measured in connection with the size of the fetal image, and the result thereof is then displayed as reference numeral 1105 (xxxx mm) of FIG. 10.

Figure 12:
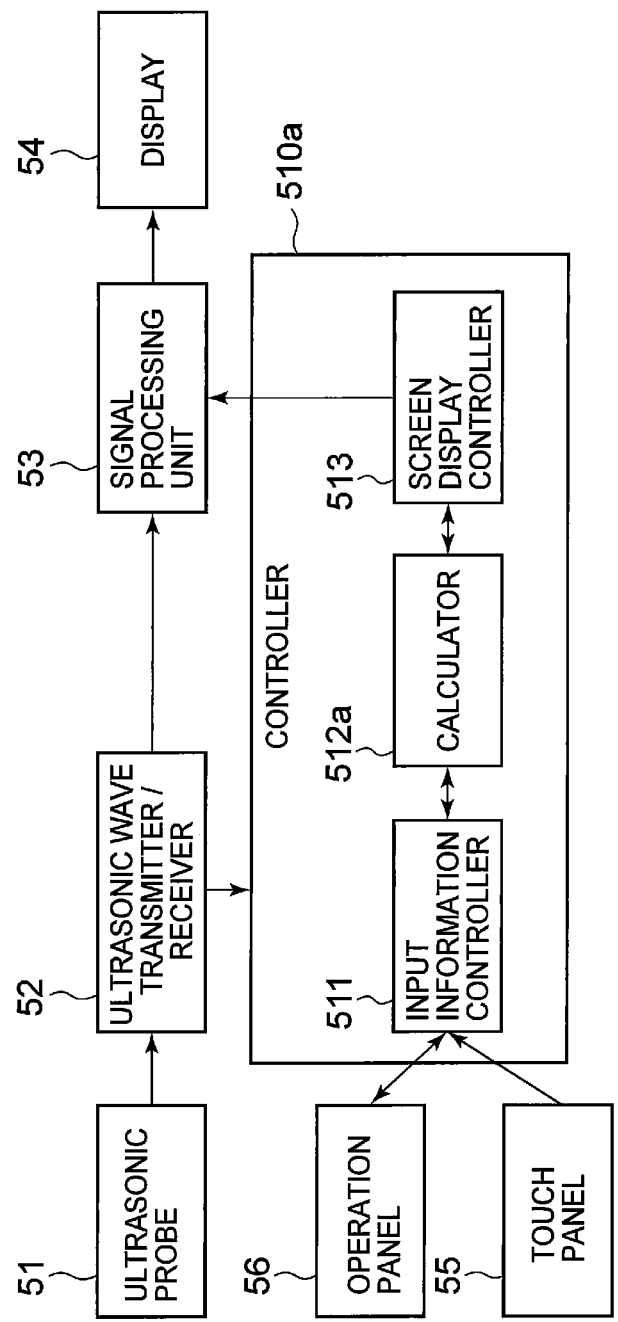
FIG. 12 is a block diagram showing a configuration of the third embodiment of the ultrasonograph according to the present invention.

FIG. 12 is a block diagram showing a configuration of the ultrasonograph executing the above measurement control. First, the touch panel-equipped display includes a display 54 and a touch panel 55. An ultrasonic wave transmitter/receiver 52 controls transmission of ultrasonic waves of an ultrasonic probe 51 and reception of reflected signals. A signal processing unit 53 processes the received reflected signal to display the ultrasonic image P in the ultrasonic image area A1 of the display 54 as shown in FIG. 10, and executes display control for displaying various operating buttons in the operating part display area A2 based on the control by a screen display controller 513. A controller 510a includes an input information controller 511, a calculator 512a, and the screen display controller 513. The input information controller 511 receives information (an event) of the user operation performed with the touch panel 55 and an operating panel 56 and processes the same. When the both ends of the head of the fetal image are specified with the cursor C, the calculator 512a especially instructs the image display controller 513 to measure the both ends of the fetal image in connection with the size of the fetal image with the cursor C and display the measurement result.

Figure 13:
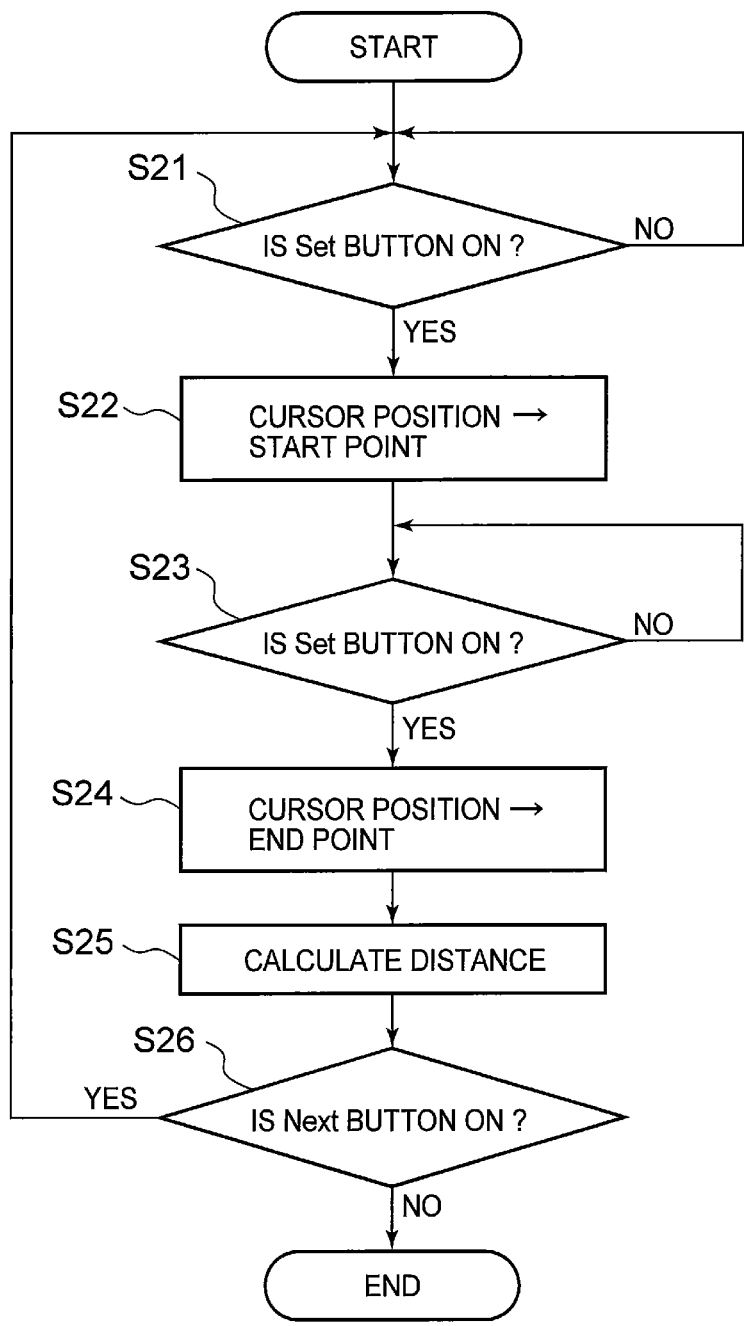
FIG. 13 is a flowchart for explaining an example of a process of the ultrasonograph of FIG. 12 according to the present invention.

FIG. 13 is a flowchart for explaining a process of the calculator 512a executing the above measurement control. When the Start button 1101 is touched, the process shown in FIG. 13 starts. First, the calculator 512a checks whether the Set button 1102 is touched (ON) (step S21). If the Set button 1102 is touched, the calculator 512a stores the current position of the cursor C as a start position (step S22).

Subsequently, the calculator 512a checks whether the Set button 1102 is touched (ON) (step S23). If the Set button 1102 is touched (ON), the calculator 512a stores the current position of the cursor C as an end position (step S24) and then measures the distance between the start and end positions in the ultrasonic image (step S25). Moreover, the calculator 512a checks whether the Next button 1103 is touched (step S26). If the Next button 1103 is touched (ON), the calculator 512a returns to the step S21, allowing measurement of distance of another region.

Figure 14:
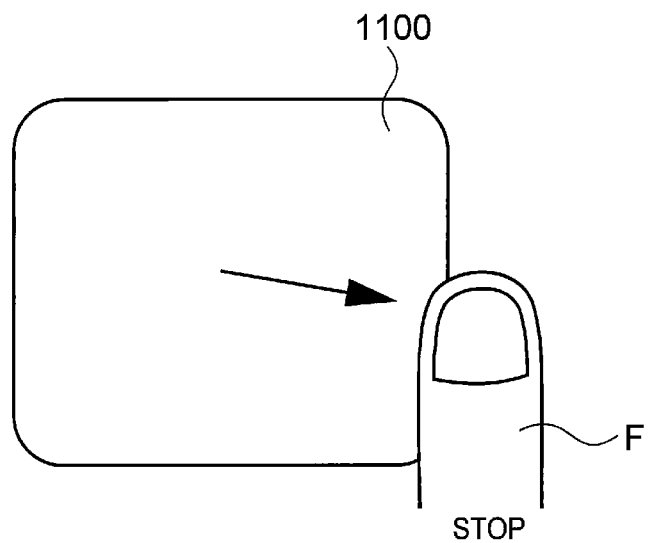
FIG. 14 is an explanatory view showing another drag operation in the touch pad area of FIG. 10.
Figure 15:
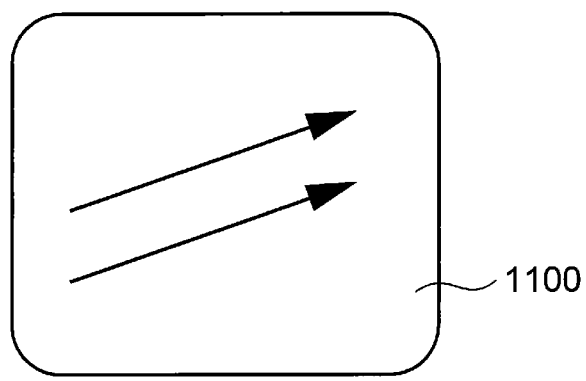
FIG. 15 is an explanatory view showing still another drag operation in the touch pad area of FIG. 10.

As another example of the drag operation, the cursor may be configured to continue moving when a drag from a drag start position within the touch pad area 1100 as shown by the finger F of FIG. 14 is continuously stopped at an edge of the touch pad area 1100. As shown in FIG. 15, the finger F (FIG. 14) is allowed to slide on the touch pad area 1100 several times in the same direction.

Fourth Embodiment

Figure 16:
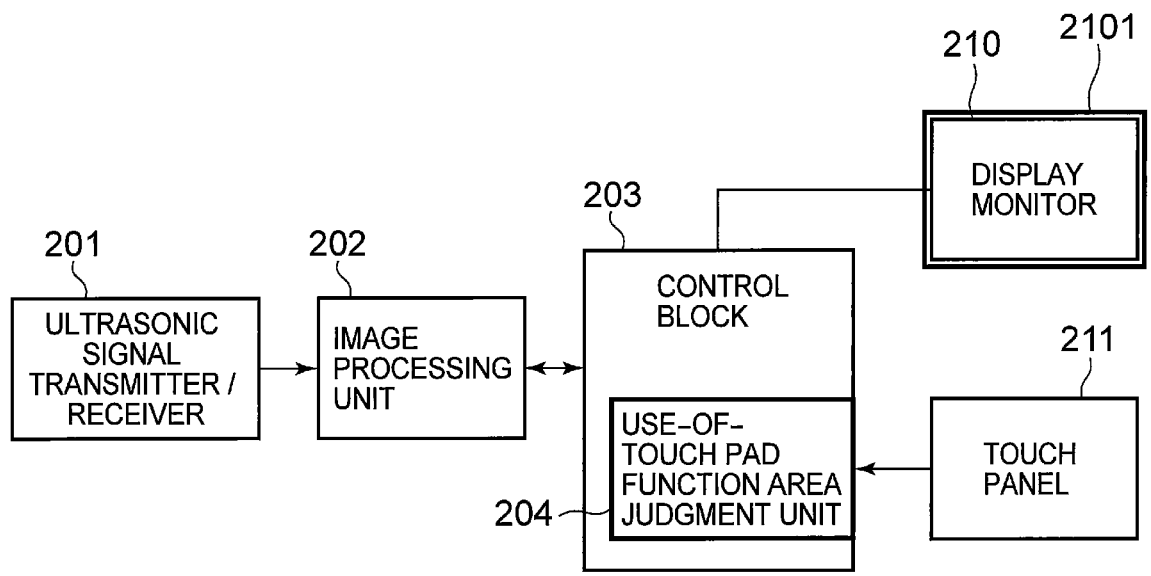
FIG. 16 is a block diagram showing an entire constitution of a fourth embodiment of the ultrasonograph of the present invention.
Figure 17:
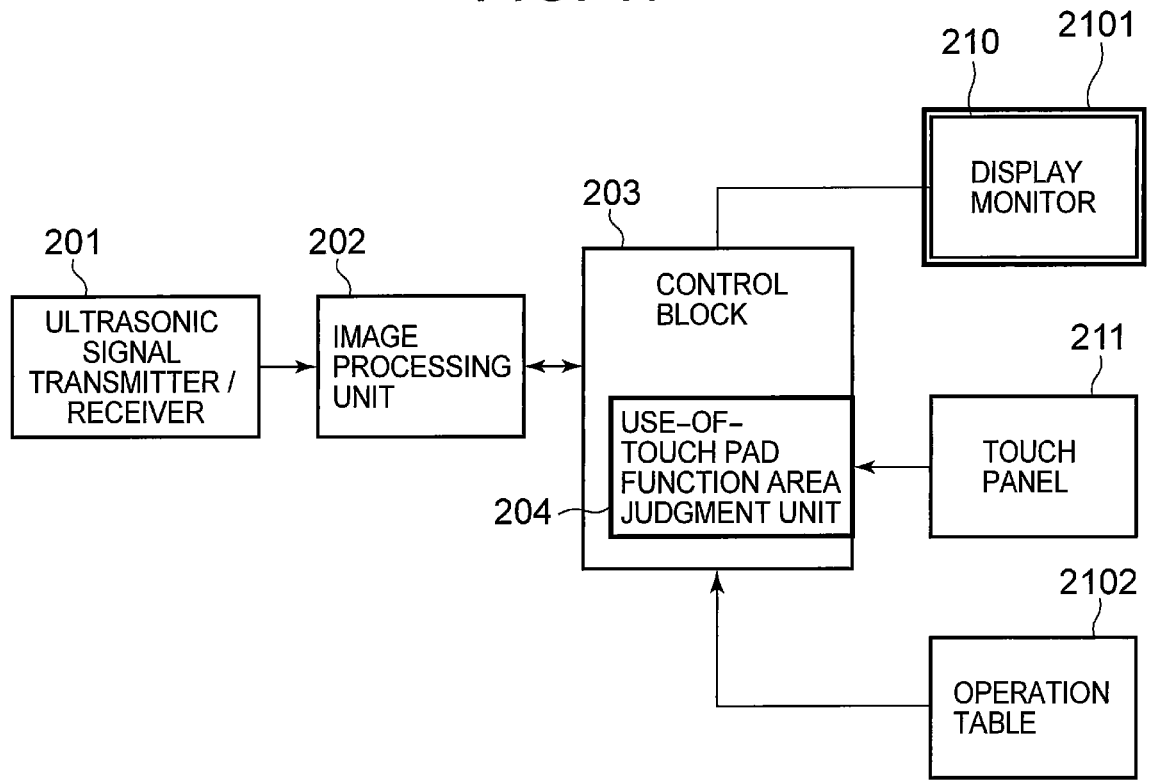
FIG. 17 is a block diagram showing a modification of the entire constitution of the fourth embodiment of the ultrasonograph of the present invention.
Figure 18:
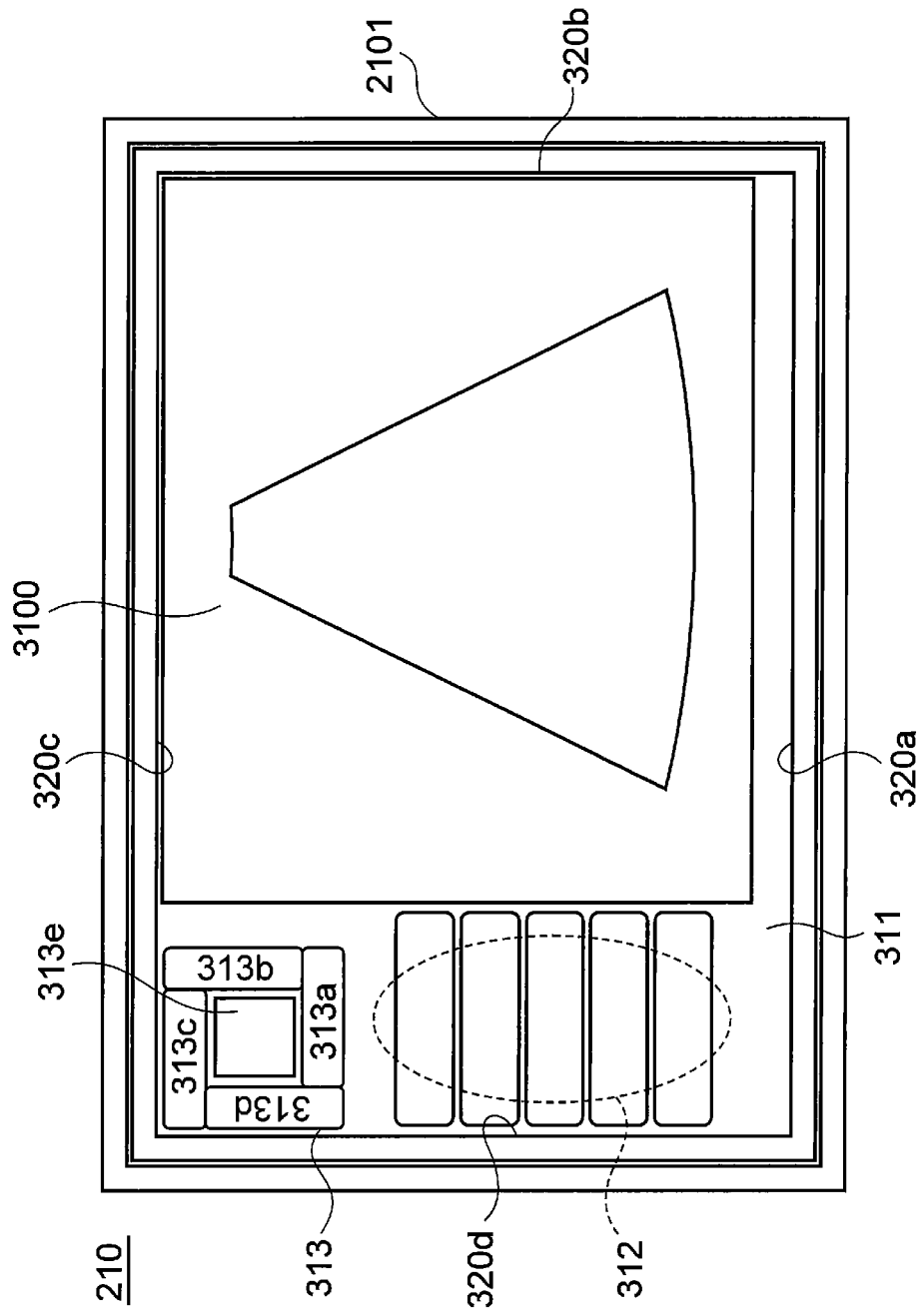
FIG. 18 is a constitutional view schematically showing a main portion of the fourth embodiment of the ultrasonograph of the present invention.

An ultrasonograph according to a fourth embodiment of the present invention is shown in FIGS. 16 to 18. In FIG. 16, the ultrasonograph according to the present invention schematically includes: an ultrasonic signal transmitter/receiver 201 transmitting an ultrasonic signal using an ultrasonic probe (not shown) to a subject (not shown) and receiving the reflected signal from the subject; an image processing unit 202 performing image processing based on the received signal or an operation signal requesting a change of the image parameters to generate an ultrasonographic image; a display monitor 210 displaying the generated ultrasonographic image; a touch panel 211 laid on the display monitor 210; and a control block 203 performing exchange of data among the processing units and performing display control for the display monitor 210. The display monitor 210 is equipped with an outer frame 2101. The touch panel 211 includes an adjacent portion which is adjacent to the inside of the outer frame 2101. The adjacent portion can be used as touch pads (independent function areas) with individual sides assignable to independent functions. The control block 203 includes a use-of-touch pad function area judgment unit 204 distinguishing use in the area having the touch pad function and use in the other area.

The touch panel 211 is not limited to being overlapped on the display monitor 210 but needs to integrally include the display function and an operation function. As shown in FIG. 17, an operating table 2102 including hard keys such as a trackball, a key switch, a slide resistor, and an encoder knob (not shown) may be also used as the input device.

FIG. 18 schematically shows a display screen of the display monitor 210. The display screen includes: an ultrasonographic screen 3100; the outer frame (hereinafter, referred to as a "display monitor frame") 2101 of the display monitor 210; an area 320 in the touch panel 211 extended in vertical and horizontal directions along four sides of the outer frame 2101 which is used as a touch pad (including portions 320a to 320d at lower, right, upper, and left sides, respectively); soft keys 312 arranged on the touch panel 211 for selection of a menu (for example, Caliper, Color, Doppler, CINE, and 2D-Live shown in FIG. 19); and soft keys 313 capable of assigning functions to the touch panel area 320 provided along the display monitor frame 2101 and displaying functions (including 313a at the bottom, 313b at the right, 313c at the top, 313d at the left, and 313e at the center).

When the operation mode of the ultrasonograph to be assigned to the soft keys 313 is selected by pressing with a finger or the like (described later), the functions as a touch pad assigned according to the selected mode is displayed at the soft keys 313 through processing by the control block 203, and the ultrasonographic screen 3100 corresponding to the selected mode is displayed. In the soft keys 313, the soft keys 313a to 313d displaying operation names corresponding to the individual sides 320a to 320d of the touch panel area 320 provided along the display monitor frame 2101 are arranged in a frame form, in which the area 313e displaying the name of the current mode or the like is provided. The names of the assigned operations can be displayed directly in the touch panel area 320 as well as in the soft keys 313. By pressing each of the soft keys 313a to 313d, the functions which can be used at the corresponding mode are displayed one after another, and the functions can be thus changed. Moreover, pressing the soft key 313e at the center changes simultaneously all the soft keys 313a to 313d at the four sides to a previously registered combination or a combination registered by the user. The positional relationship between the ultrasonographic screen 3100 and the soft keys 312 and 313, the shape and arrangement of the soft keys 312 and 313, and the shape of the display monitor 210 are not limited to those shown in FIG. 18 and may be different from those shown in FIG. 18 as long as the same functions are implemented.

According to the above-described ultrasonograph of the fourth embodiment of the present invention, providing the touch panel area 320 extending vertically and horizontally along the display monitor frame 2101 allows the operator to easily adjust the entry speed and position, thus enabling the input through various institutive operation ways. Moreover, by providing the soft keys 313 for selection of the functions of the touch panel area 320, the functions assigned to the touch panel area 320 can be changed simultaneously or individually. Furthermore, by displaying the function currently assigned to the touch panel area 320, the operator is prevented from performing incorrect operations. Still furthermore, by arranging the soft keys 312 capable of changing modes on the same screen, the finger movement at the mode change operation can be reduced, thus improving the overall operability of the ultrasonograph.

Figure 19:
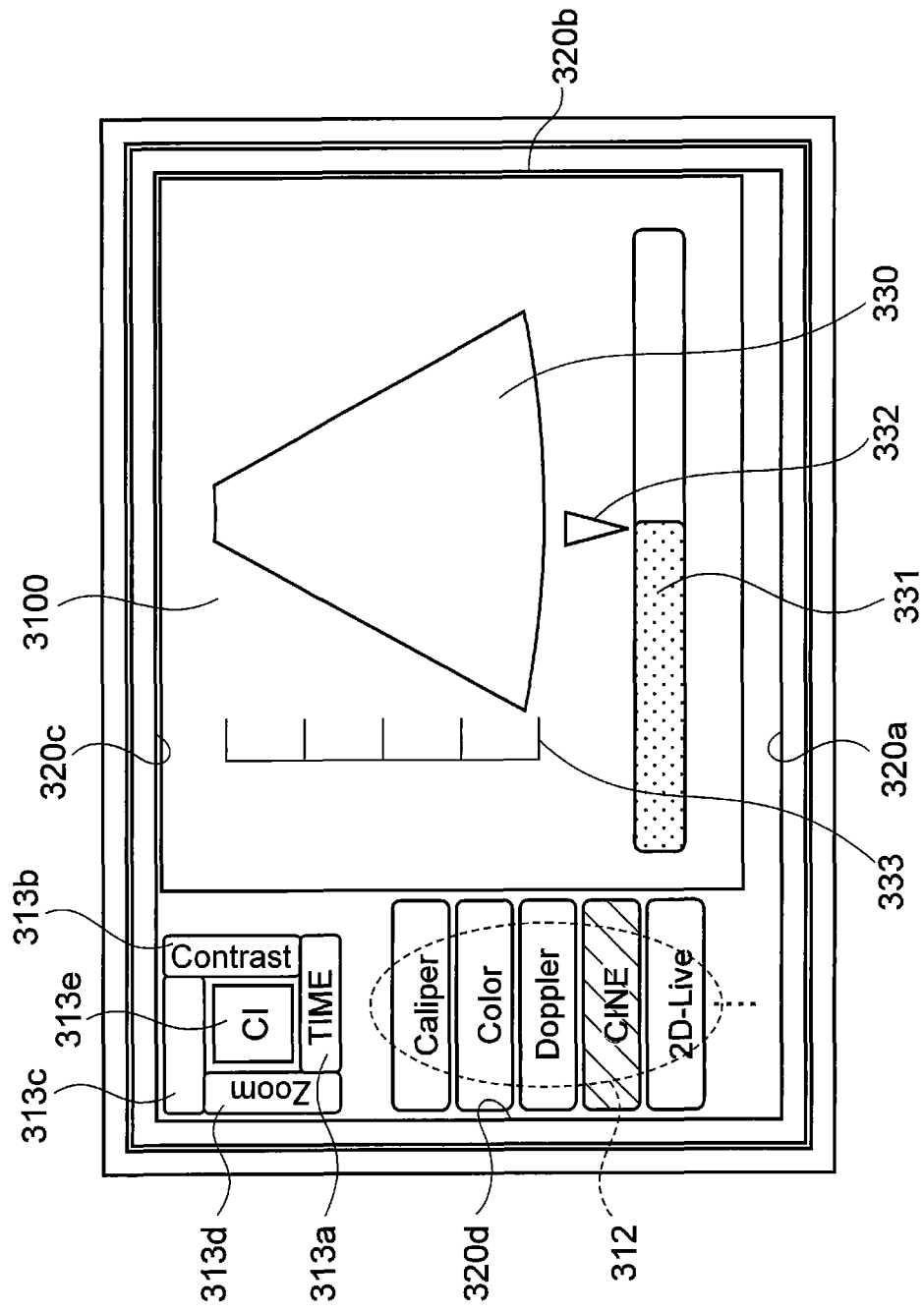
FIG. 19 is an explanatory view of an operation in which when the fourth embodiment of the present invention is implemented in a CINE play mode, a parameter setting operation is performed in a touch panel area adjacent to a monitor frame.

Next, FIG. 19 shows a concrete example of the ultrasonograph of the fourth embodiment of the present invention. FIG. 19 shows a screen for a CINE play mode playing diagnostic video stored as a series of images in the ultrasonograph. In the soft keys 312, the soft key of the current mode (CINE) is selected, and the name of the current mode (CI) is displayed at the soft key 313e at the center of the soft key 313. The ultrasonographic screen 3100 displays: an ultrasonic image 330; a CINE play bar 331 indicating length of the entire series of stored images; a pointer 332 indicating a current display position in the CINE play bar 331; a scale 333; and the like. The touch panel areas 320a to 320d provided along the display monitor frame 2101 are assigned to the functions displayed at the soft keys 313a to 313d (TIME, Contrast, none, and Zoom), respectively.

Figure 20:
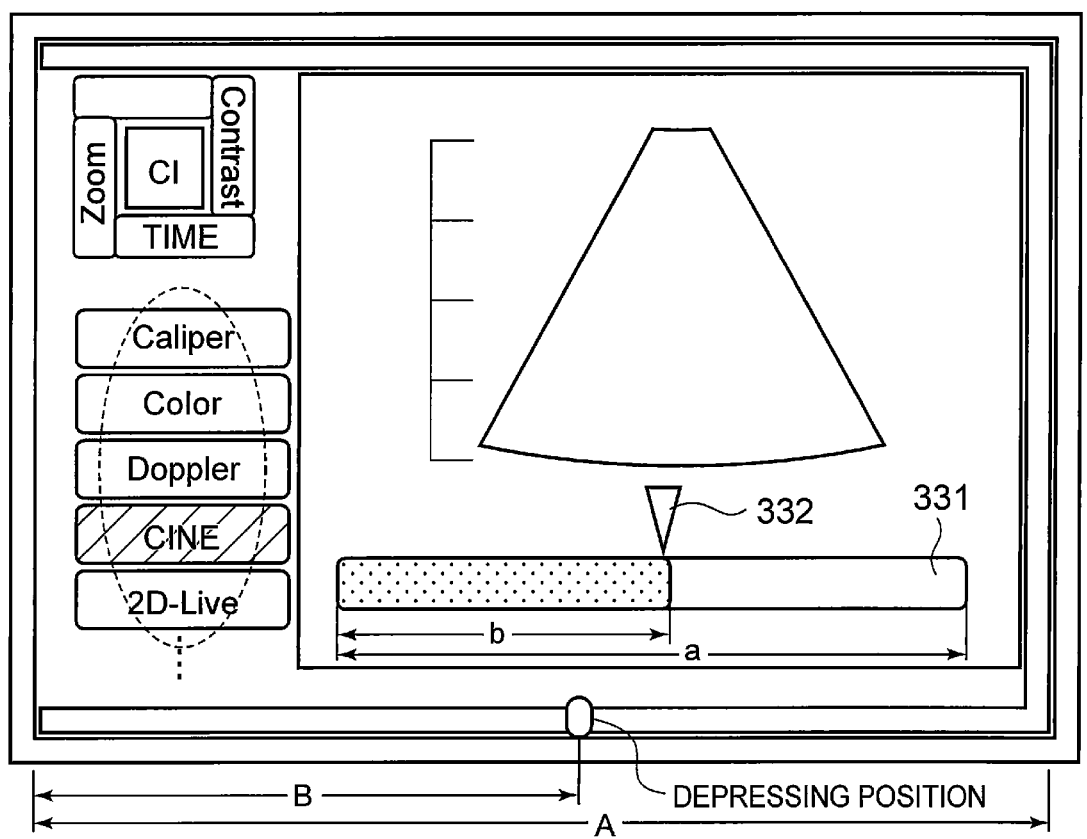
FIG. 20 is an explanatory view of an example of CINE play in FIG. 19 (where the touch pad shows position).

For example, to flick the series of images chronologically forward and backward chronological order, the touch panel area 320a at the lower side corresponding to the soft key 313a marked "TIME" needs to be pressed or scrolled in the horizontal direction with a finger or the like. At this time, in one of the ways of implementing the same, the horizontal length of the touch panel area 320a is related to the entire length of the series of images (N images). As shown in FIG. 20, a position b of a pointer 332 is determined so that a/b equals to N/B where: B is the depressing position with the origin at the left end of the touch panel area 320a; A, the length of the touch panel area 320a; b, the position of the pointer 332 with the origin at the left end of the CINE play bar 331; and a, the length of the CINE play bar. An N×(B/A)-th image is set to the current image. Furthermore, scrolling speed or acceleration is detected and is directly reflected on speed or acceleration at which the images are flicked forward or backward. With the above specification, the operator can institutively control display of images.

Figure 21:
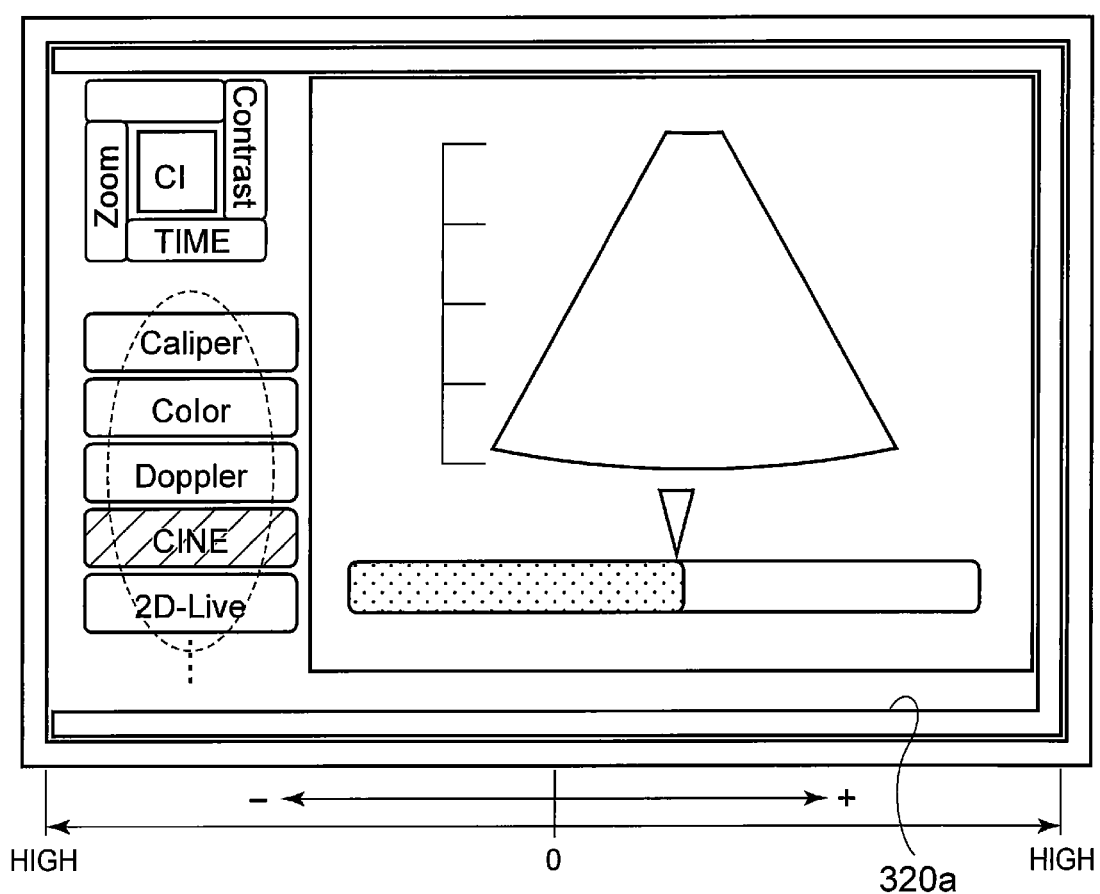
FIG. 21 is an explanatory view of an example of CINE play in FIG. 19 (where the touch pad shows speed).

In another implementation way thereof, the speed at which the images are flicked is displayed in the touch panel area 320a. As shown in FIG. 21, with the center of the touch panel area 320a being set to a speed of zero, the right and left sides thereof denote positive and negative speeds, respectively, and the distance from the center denotes the magnitude of relative speed. This allows the operator to continuously and stably control the image flicking speed at the pressing position. All of the aforementioned process is performed through the control block 203.

The similar process is performed in the case of vertically sliding a finger or the like on the touch panel area 320d at the left side with a finger or the like. The corresponding soft key 313d is assigned to the "Zoom" function in this case. A scale 333 and ultrasonic image 330 can be therefore continuously zoomed in and out through the control block 203 in conjunction with the movement of the finger or the like.

Similarly, in the case of vertically sliding the finger or the like on the touch panel area 320b at the right side, the corresponding soft key 313b is assigned to the "Contrast" function, and the contrast of the display monitor 210 is changed. When the contrast has continuous values, the contrast can be set in the same way as the above description. In the case where the contrast has discrete values, the touch panel area 320b is virtually divided by the number of available discrete values into equal sections, and the contrast can be set to each discrete value depending on the depressing position, by use of the control block 203.

The touch panel area 320c at the upper side corresponding to the soft key 313c not marked with any function is not assigned to any function. In such a case, operations for the touch panel 320c are disabled.

Figure 22:
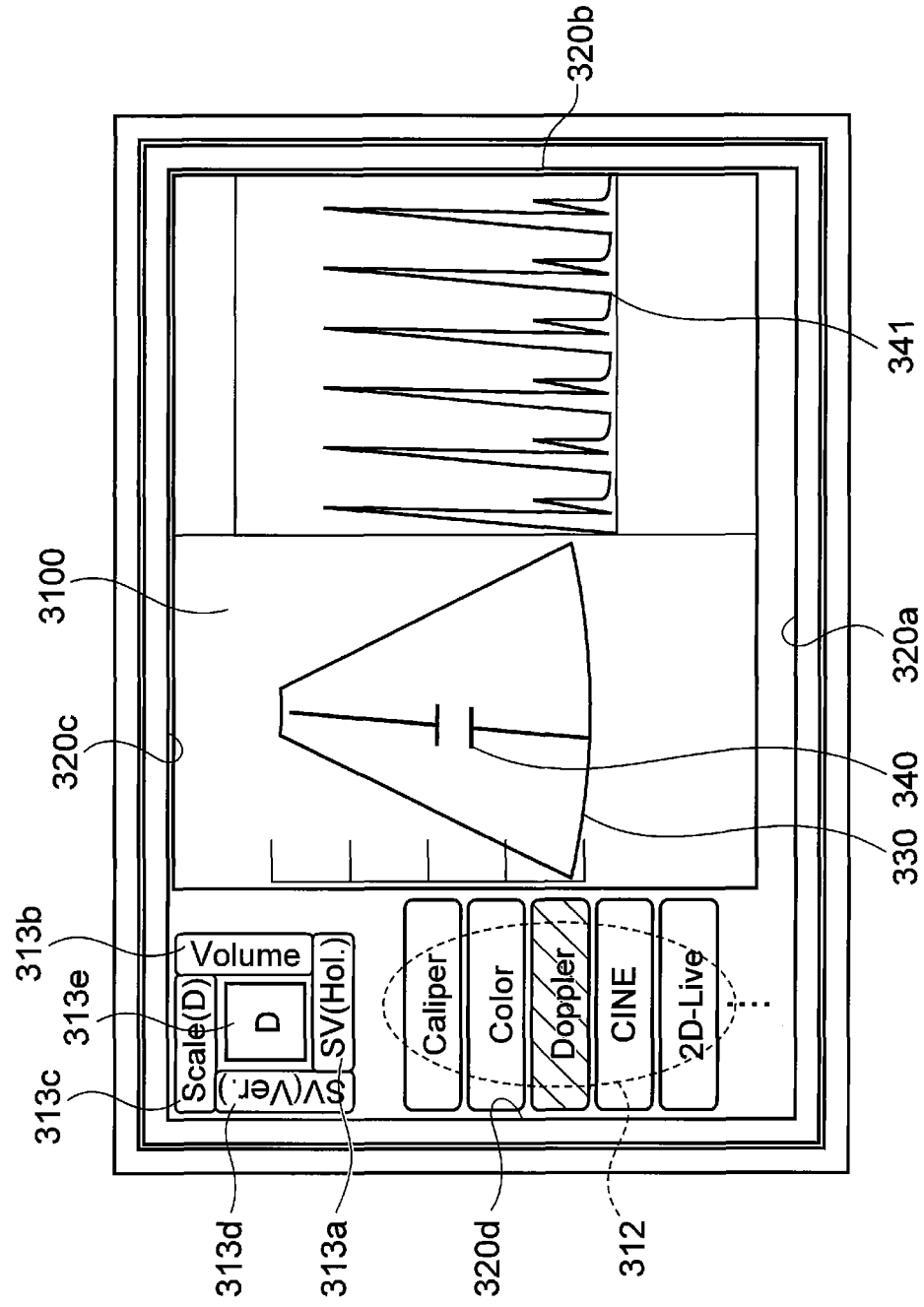
FIG. 22 is an operation explanatory view in which when the fourth embodiment of the present invention is implemented in a Doppler mode, the parameter setting operation is performed in the touch panel area adjacent to the monitor frame.
Figure 23:
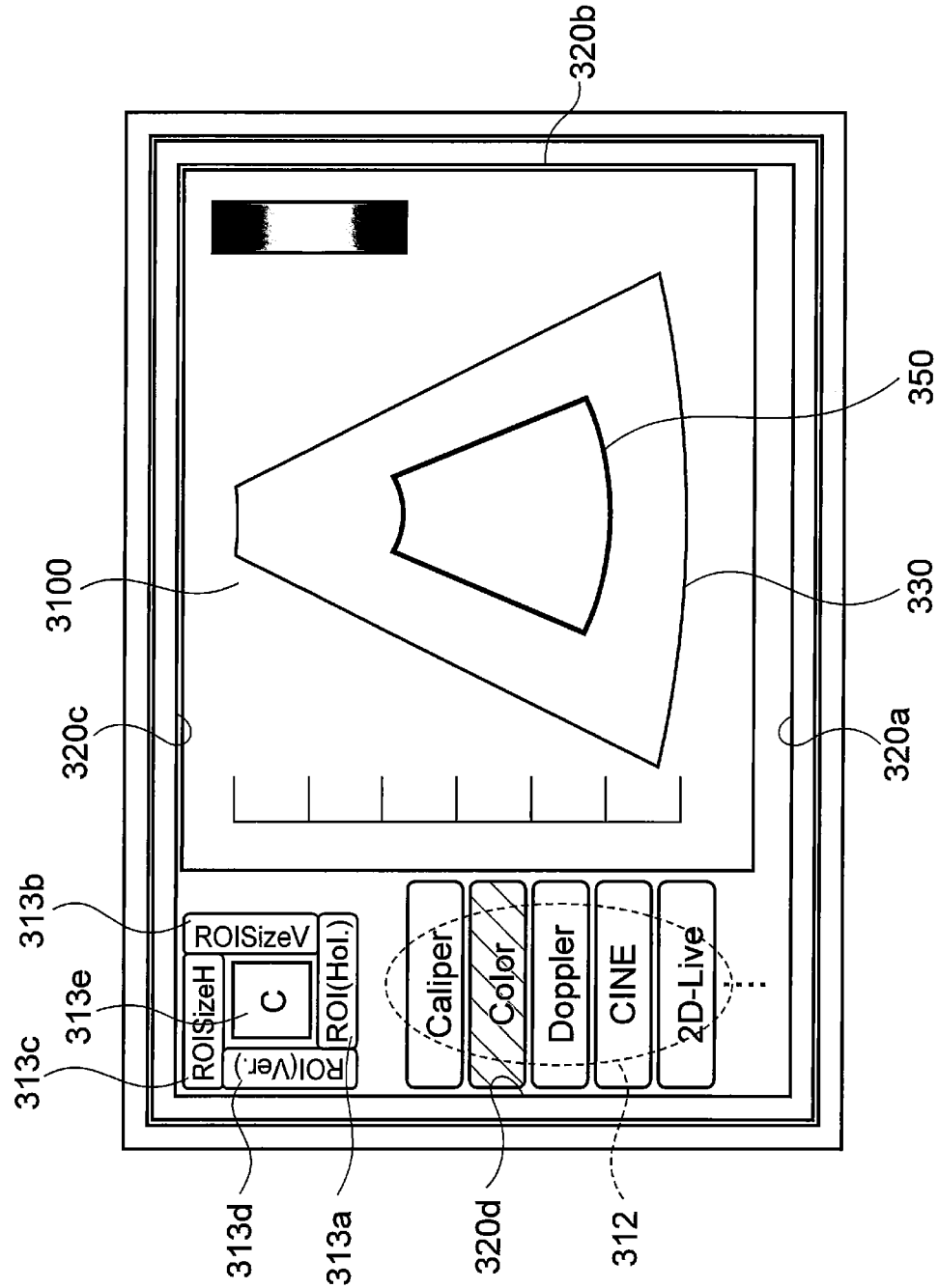
FIG. 23 is an operation explanatory view in which when the fourth embodiment of the present invention is implemented in a Color mode, the parameter setting operation is performed in the touch panel area adjacent to the monitor frame.
Figure 24:
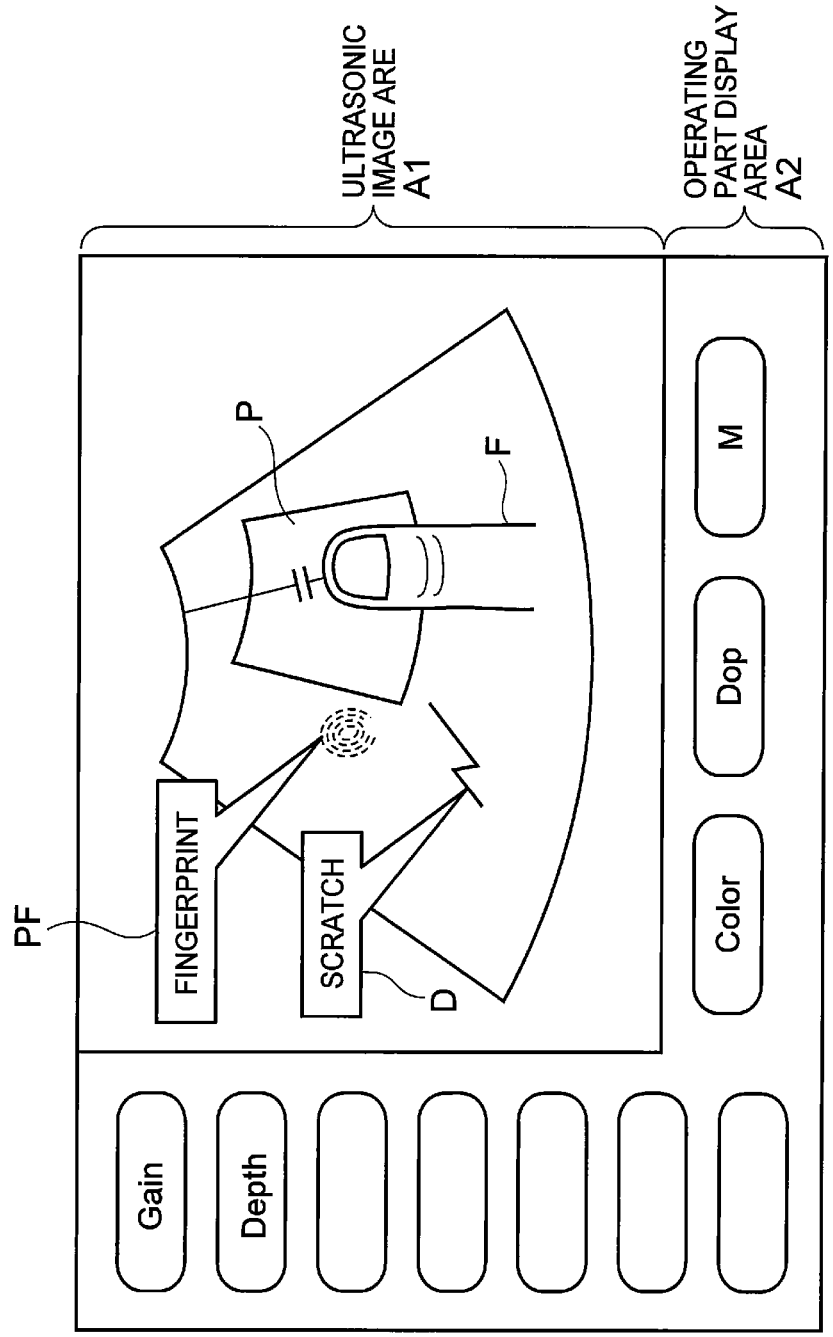
FIG. 24 is an explanatory view showing a display example a conventional ultrasonograph.

FIGS. 22 and 23 show examples of other major functions of the ultrasonograph to which the fourth embodiment is applied. FIG. 22 shows a screen at the Doppler mode in which the blood flow velocity at the position indicated by a sample volume in the image and the like are measured. The soft key 312 corresponding to the current mode "Doppler" is selected, and the name (D) of the current mode is displayed at the soft key 313e at the center of the soft keys 313. In the left half of the ultrasonographic screen 3100, a sample volume 340 is displayed in addition to the ultrasonic image 330. In the right half, strength 341 of the blood flow (in the vertical axis) is displayed along the time axis (the horizontal axis). The touch panel areas 320a to 320d along the display monitor frame 2101 are assigned to the functions (SV(Hol.), Volume, Scale(D), and SV(Ver)) marked at the soft keys 313a to 313d, respectively. For example, when a finger or the like slides on the touch panel area 320a at the lower side or the touch panel area 320d at the left side in the horizontal or vertical direction, respectively, the position of the sample volume 340 is continuously moved in a horizontal or vertical direction through the same process as that in the case of FIG. 19 since the corresponding soft keys 313a and 313d are assigned to "SV (Horizontal)" and "SV (Vertical)", respectively.

FIG. 23 shows a color-mode screen visualizing the direction of blood flow within ROI (Region of Interest) 350 in different colors. The soft key 312 corresponding to the current mode (Color) is selected, and the name (C) of the current mode is displayed at the soft key 313e. The ultrasonographic screen 3100 displays the ROI 350 in addition to the ultrasonic image 330. The touch panel areas 320a to 320d provided along the display monitor frame 2101 are assigned to the functions (ROI(Hol.), ROIsizeV, ROISizeH, and ROI(Ver.)) marked at the soft keys 313a to 313d, respectively.

For example, when a finger or the like slides on the touch panel area 320a at the lower side or the touch panel area 320d at the left side in the horizontal or vertical direction, respectively, the position of the ROI 350 is continuously moved in a horizontal or vertical direction through the same process as that in the case of FIG. 19 since the corresponding soft keys 313a and 313d are assigned to "ROI (Horizontal)" and "ROI (Vertical)", respectively. Moreover, when a finger or the like slides on the touch panel area 320b at the right side or the touch panel area 320c at the upper side in the vertical or horizontal direction, respectively, the size of the ROI 350 is continuously changed in a horizontal or vertical direction since the corresponding soft keys 313b and 313c are assigned to "ROI Size vertical" and "ROI Size Horizontal", respectively. The size of the ROI 350 may be changed by depressing the touch panel area 320 at two points with fingers or the like, changing the relative distance between the two depressing points, and reflecting the relative distance in the size of the ROI 350.

According to the ultrasonograph of the fourth embodiment of the present invention, it is possible to easily change the parameters having discrete or continuous values by detecting the relative or absolute position of the depressed point when input is performed using the touch panel area 320 provided along the monitor frame 2101 or, for scrolling, by detecting the moving speed or acceleration and furthermore the relative or absolute amount of the movement thereof.

The functional blocks used for explanation of the aforementioned embodiments are typically implemented as LSIs which are integrated circuits. These may be individually integrated into one chip or may be integrated into one chip including a part or all of the functions. Herein, the integrated circuits for implementing functional blocks are LSIs but may be ICs, system LSIs, super LSIs, or ultra-LSIs depending on the integration thereof. Moreover, the method for integration is not limited to LSIs and may be implemented with a dedicated circuit or a general-purpose processor. Furthermore, an FPGA (Field Programmable Gate Array), which is programmable after manufacturing the LSI, or a reconfigurable processor which can reconfigure the connection or settings of circuit cells in the LSI may be used. Furthermore, if an circuit integration technology substitutable for LSIs comes up with the progress of the semiconductor technology or another derived technology, it should be understood that the function blocks may be integrated using the technology.

INDUSTRIAL APPLICABILITY

The present invention can prevent a part of a touch panel-equipped display which displays an ultrasonic tomographic image from getting dirty with fingerprints or scratches when a drag operation is used to change the displayed content of the ultrasonic tomographic image displayed on the touch panel-equipped display. The present invention therefore has an effect on making the ultrasonic tomographic image more visible and can be applied to ultrasonographs and the like.

The ultrasonograph according to the present invention allows a part of the touch panel area along the monitor frame to be treated as a touch pad, the touch panel area being laid on a monitor. The input for the ultrasonograph is performed with a finger or a tool along the monitor frame in the part provided along the monitor frame, thus facilitating control of the input speed and position. The ultrasonograph according to the present invention therefore has another effect on allowing input to be performed by various institutive operation ways and is useful as an ultrasonograph with the image parameters changeable by the user or the like.

The invention claimed is:
1. An ultrasonograph comprising:
   an image processing circuit configured to generate an ultrasonic image based on an ultrasonic signal from an ultrasonic probe;
   a control circuit; and
   a display comprising:
      a first display area;
      a second display area; and
      a touch panel that is provided at least in the second display area, the second display area comprising a touch pad area that is displayed at a same constant position and in a same constant size in the second display area during a drag operation;
   wherein the control circuit is configured to control the display to display the ultrasonic image and a cursor in the first display area only;
   wherein the control circuit controls the display to display, in the second display area, the touch pad area on which the drag operation is performed to move the cursor displayed on the ultrasonic image in the first display area, the drag operation comprising a drag motion;
   wherein the control circuit continues to move the cursor displayed in the first display area when the drag motion enters an area of the second display area that is outside of the touch pad area.

* * * * *